(12) United States Patent
Shapiro

(10) Patent No.: US 6,489,308 B1
(45) Date of Patent: Dec. 3, 2002

(54) INHIBITORS OF SERINE PROTEASE ACTIVITY, METHODS AND COMPOSITIONS FOR TREATMENT OF NITRIC-OXIDE-INDUCED CLINICAL CONDITIONS

(75) Inventor: Leland Shapiro, Denver, CO (US)

(73) Assignee: Trustees of University of Technology Corporation, Boulder, CO (US)

(*) Notice: Subject to any disclaimer, the term of this patent is extended or adjusted under 35 U.S.C. 154(b) by 0 days.

(21) Appl. No.: 09/518,097

(22) Filed: Mar. 3, 2000

Related U.S. Application Data

(60) Provisional application No. 60/123,167, filed on Mar. 5, 1999, and provisional application No. 60/156,523, filed on Sep. 29, 1999.

(51) Int. Cl.⁷ .................... A61K 31/70; A61K 31/35; A61K 31/40; A61K 31/16
(52) U.S. Cl. .................... 514/45; 514/454; 514/423; 514/613
(58) Field of Search .................... 514/458, 455, 514/456, 423, 45, 454, 613

(56) References Cited

U.S. PATENT DOCUMENTS

| | | |
|---|---|---|
| 4,021,472 A | 5/1977 | Fujii et al. |
| 4,051,842 A | 10/1977 | Hazel et al. |
| 4,140,122 A | 2/1979 | Kuhl et al. |
| 4,224,342 A | 9/1980 | Fujii et al. |
| 4,283,418 A | 8/1981 | Fuji et al. |
| 4,310,533 A | 1/1982 | Uegai et al. |
| 4,383,529 A | 5/1983 | Webster |
| 4,629,567 A | 12/1986 | Bollen et al. |
| 4,657,763 A * | 4/1987 | Finkelstein ............ 424/649 |
| 4,668,504 A | 5/1987 | Kahan et al. |
| 4,711,848 A | 12/1987 | Insley et al. |
| 4,713,224 A | 12/1987 | Tamhankar et al. |
| 4,732,973 A | 3/1988 | Barr et al. |
| 4,760,130 A | 7/1988 | Thompson et al. |
| 4,788,603 A | 11/1988 | Fujimura et al. |
| 4,829,052 A | 5/1989 | Glover et al. |
| 4,839,283 A | 6/1989 | Kawasaki et al. |
| 4,843,094 A | 6/1989 | Imaki et al. |
| 4,889,723 A | 12/1989 | Kim et al. |
| 4,931,279 A | 6/1990 | Bawa et al. |
| 4,963,654 A | 10/1990 | Katunuma |
| 5,004,612 A | 4/1991 | Kim et al. |
| 5,077,428 A | 12/1991 | Imaki et al. |
| 5,110,602 A | 5/1992 | Kim et al. |
| 5,157,019 A | 10/1992 | Glover et al. |
| 5,166,134 A * | 11/1992 | Lezdey et al. .......... 514/8 |

(List continued on next page.)

FOREIGN PATENT DOCUMENTS

| | | |
|---|---|---|
| WO | WO94/07525 A | 4/1994 |
| WO | WO95/28422 | 10/1995 |
| WO | WO95/34538 | 12/1995 |
| WO | WO96/12021 | 4/1996 |
| WO | WO96/14067 | 5/1996 |
| WO | WO 97/03679 | 2/1997 |
| WO | WO97/09346 | 3/1997 |
| WO | WO97/09347 | 3/1997 |
| WO | WO97/10222 | 3/1997 |
| WO | WO 97/10231 | 3/1997 |
| WO | WO 97/21690 | 6/1997 |
| WO | WO 97/24339 | 7/1997 |
| WO | WO97/31937 | 9/1997 |
| WO | WO 97/33996 | 9/1997 |
| WO | WO 97/37969 | 10/1997 |
| WO | WO 97/45402 | 12/1997 |
| WO | WO 97/48706 | 12/1997 |
| WO | WO 97/49679 | 12/1997 |
| WO | WO98/06417 | 2/1998 |
| WO | WO98/09206 | 3/1998 |
| WO | WO 98/20034 | 5/1998 |
| WO | WO 98/21186 | 5/1998 |
| WO | WO 98/22098 | 5/1998 |
| WO | WO 98/22619 | 5/1998 |
| WO | WO 98/23565 | 6/1998 |
| WO | WO 98/24806 | 6/1998 |
| WO | WO 98/46597 | 10/1998 |
| WO | WO98/49190 | 11/1998 |
| WO | WO 98/50342 | 11/1998 |
| WO | WO 98/50420 | 11/1998 |
| WO | WO 98/56821 | 12/1998 |
| WO | WO 97/41231 | 8/1999 |
| WO | WO 99/43308 | 9/1999 |
| WO | WO00/52034 | 9/2000 |

OTHER PUBLICATIONS

Aoki H, Akaike T, Abe K, Kuroda M, Arai S, Okamura R, Negi A, Maeda H. Antiviral effect of oryzacystatin, a proteinase inhibitor in rice, against herpes simplex virus type I in vitro and in vivo. Antimicrob Agents Chemother Apr. 1995; 39(4):846–9.

Auerswald et al., "Recombinant leech–derived tryptase inhibitor: construction, production, protein chemical characterization and inhibition of HIV–1 replication", Biol Chem Hoppe Seyler, 375(10):695–703 (1994).

Avril LE, Di Martino–Ferrer M, Barin F, Gauthier F., "Interaction between a membrane–associated serine proteinase of U–937 monocytes and peptides from the V3 loop of the human immunodeficiency virus type I (HIV–1) gp120 envelope glycoprotein", FEBS Lett, 317(1–2):167–72 (Feb. 8, 1993).

(List continued on next page.)

*Primary Examiner*—Zohreh Fay
*Assistant Examiner*—Vickie Kim
(74) *Attorney, Agent, or Firm*—Katten Muchin Zavis Rosenman

(57) ABSTRACT

A novel method of treating and preventing diseases is provided. In particular, compositions and methods of blocking diseases associated with aberrant levels of nitric oxide and facilitated by a serine proteolytic (SP) activity are disclosed, which consist of administering to a subject a therapeutically effective amount of a compound having a serine protease inhibitory activity. Among effective compounds are $\alpha_1$-antitrypsin and synthetic drugs mimicking some or all of the actions of $\alpha_1$-antitrypsin.

2 Claims, 6 Drawing Sheets

U.S. PATENT DOCUMENTS

| | | |
|---|---|---|
| 5,175,253 A | 12/1992 | Fallon et al. |
| 5,214,191 A | 5/1993 | Kirschenheuter et al. |
| 5,216,022 A | 6/1993 | Oleksyszyn et al. |
| 5,240,956 A | 8/1993 | Kirschenheuter et al. |
| 5,247,084 A | 9/1993 | Imaki et al. |
| 5,281,617 A | 1/1994 | Kirschenheuter et al. |
| 5,314,910 A | 5/1994 | Kirschenheuter et al. |
| 5,376,655 A | 12/1994 | Imaki et al. |
| 5,399,346 A | 3/1995 | Anderson et al. |
| 5,416,191 A | 5/1995 | Cheronis et al. |
| 5,420,110 A | 5/1995 | Miller et al. |
| 5,432,178 A | 7/1995 | Nakai et al. |
| 5,470,970 A | 11/1995 | Saeger et al. |
| 5,476,995 A | 12/1995 | Clark et al. |
| 5,478,727 A | 12/1995 | Roizman et al. |
| 5,486,470 A | 1/1996 | Darke et al. |
| 5,489,593 A * | 2/1996 | Palmer et al. ............... 514/542 |
| 5,504,094 A * | 4/1996 | Nakane et al. ............... 514/360 |
| 5,514,653 A | 5/1996 | Perlmutter |
| 5,514,713 A | 5/1996 | Nakai et al. |
| 5,529,920 A | 6/1996 | Cole et al. |
| 5,532,215 A | 7/1996 | Lezdey et al. |
| 5,565,334 A | 10/1996 | Kufe et al. |
| 5,567,682 A * | 10/1996 | Pert ............................ 514/15 |
| 5,593,858 A | 1/1997 | Fleer et al. |
| 5,604,201 A | 2/1997 | Thomas et al. |
| 5,610,140 A | 3/1997 | Goodfellow et al. |
| 5,610,285 A | 3/1997 | Lebing et al. |
| 5,614,555 A | 3/1997 | Nakai et al. |
| 5,616,693 A | 4/1997 | Hwang et al. |
| 5,618,792 A | 4/1997 | Gyorkos et al. |
| 5,622,984 A | 4/1997 | Nakai et al. |
| 5,635,593 A | 6/1997 | Cheronis et al. |
| 5,641,670 A | 6/1997 | Treco et al. |
| 5,663,416 A | 9/1997 | Kirschenheuter et al. |
| 5,665,589 A | 9/1997 | Harris et al. |
| 5,700,779 A | 12/1997 | Goodfellow et al. |
| 5,710,026 A | 1/1998 | Sprecher |
| 5,712,117 A | 1/1998 | Sprecher |
| 5,747,645 A | 5/1998 | Sprecher |
| 5,750,506 A | 5/1998 | Goodfellow et al. |
| 5,759,548 A | 6/1998 | Bathurst et al. |
| 5,780,009 A | 7/1998 | Karatzas et al. |
| 5,798,442 A | 8/1998 | Gallant et al. |
| 5,801,148 A | 9/1998 | Gyorkos et al. |
| 5,804,594 A * | 9/1998 | Murad ........................ 514/474 |
| 5,807,829 A | 9/1998 | Gyorkos et al. |
| 5,811,241 A | 9/1998 | Goodfellow et al. |
| 5,817,484 A | 10/1998 | Yu et al. |
| 5,834,431 A | 11/1998 | Stewart et al. |
| 5,843,900 A | 12/1998 | Cheronis et al. |
| 5,849,863 A | 12/1998 | Stewart et al. |
| 5,861,299 A | 1/1999 | Archibald et al. |
| 5,861,380 A | 1/1999 | Gyorkos et al. |
| 5,863,899 A | 1/1999 | Cheronis et al. |
| 5,869,455 A | 2/1999 | Gyorkos et al. |
| 5,874,424 A | 2/1999 | Batchelor et al. |
| 5,874,585 A | 2/1999 | Gyorkos et al. |
| 5,891,852 A | 4/1999 | Gyorkos et al. |
| 5,914,342 A * | 6/1999 | Maurer et al. ............... 514/597 |
| 6,127,356 A * | 10/2000 | Crapo et al. |
| 6,140,116 A * | 10/2000 | Dinsmore et al. .......... 435/325 |
| 6,235,714 B1 * | 5/2001 | Paul et al. |
| 6,323,219 B1 * | 11/2001 | Costanzo |

OTHER PUBLICATIONS

Beal, M.F., "Mitochondria, Free Radicals, and Neurodegeneration", *Curr. Opin. Neurobiol.*, 1996, 6, 661–666.

Bjorck L, Grubb A, Kjellen L. Cystatin C, a human proteinase inhibitor, blocks replication of herpes simplex virus. J Virol Feb. 1990;64(2):941–3.

Carroccio A, Fontana M, Spagnuolo MI, Zuin G, Montalto G, Canani RB, Verghi F, Di Martino D, Bastoni K, Buffardi F, Guarino A., "Pancreatic dysfunction and its association with fat malabsorption in HIV infected children", Gut, 43(4):558–63 (Oct. 1998).

Cox et al., "Synergistic combinations and peptides in the inhibition of human immunodeficiency virus", Adv Enzyme Regul, 31:85–97 (1991).

Deigner, H.P. and R. Kinscherf, "Modulating Apoptosis: Current Applications and Prospects for Future Drug Development", Curr Med *Chem* 1999, 6, 399–414.

DiIanni CL, Drier, DA, Deckman IC, McCann PJ 3d, Liu F, Roizinan B, Colonno RJ, Cordingley MG. Identification of the herpes simplex virus–I protease cleavage sites by direct sequence analysis of autoproteolytic cleavage products. Biol Chem Jan. 25, 1993;268(3):2048–51.

DiIanni CL, Stevens JT, Bolgar M, O'Boyle DR 2nd, Weinheimer SP, Colonno RJ. Identification of the serine residue at the active site of the herpes simplex virus type 1 protease. J Biol Chem Apr. 29, 1994;269(17):12672–6.

Flaitz CM, Hicks MJ. "Molecular piracy: the viral link to carcinogenesis." Oral Oncol Nov. 1998;34(6):448–53.

Griffin, William C., "Calculation of HLB Values of Non-Ionic Sufactants", [H. L. B.—The Hydrophilic–Lipophilic Balance], J. Soc. Cos. Met. Chem., vol. 5, p. 249 (1954).

Holwerda BC. Herpesvirus proteases: targets for novel antiviral drugs. Antiviral Res Jun. 1997;35(1):1–21.

Inocencio et al., "Endoprotease activities other than furin and PACE4 with a role in processing of HIV–I gp160 glycoproteins in CHO–K1 cells", J Biol Chem, 272(2):1344–8 (1997).

Jabs, Thorsten, "Reactive Oxygen Intermediates as Mediators of Programmed Cell Death in Plants and Animals", *Biochem Pharmacol* 1999, 57, 231–245.

Kaufmann, Scott H., Serge Desnoyers, Yvonne Ottaviano, Nancy E. Davidson, and Guy G. Poirier, "Specific Proteolytic Cleavage of Poly(ADP–ribose) Polymerase: An Early Marker of Chemotherapy–induced Apoptosis", Cancer Res 1993, 53, 3976.

Kidd, Vincent J., Proteolytic Activities That Mediate Apoptosis, *Annu Rev Physiol,* 1998, 60, 533.

Kido H, Niwa Y, Beppu Y, Towatari T. Cellular proteases involved in the pathogenicity of enveloped animal viruses, human immunodeficiency virus, influenza virus A and Sendai virus. Adv Enzyme Regul 1996;36–325–47.

Best, P.J.M., et al., *Arterioscler Thromb Vasc Biol* 1999, 19, 14.

Lomas DA, Elliott PR, Carrell RW. Commercial plasma alphal–antitrypsin (Prolastin) contains a conformationally inactive, latent component. Eur. Respir J Mar. 1997;10(3):672–5.

Meylan et al., "HIV infectivity is not augmented by treatment with trypsin, Factor Xa or human mast–cell tryptase", AIDS, 6(1):128–30 (1992).

Miranda et al., "Isolation of the human PC6 gene encoding the putative host protease for HIV–1 gp160 processing in CD4+ T lymphocytes", Proc Natl Acad Sci U S A, 93(15):7695–7700) (1996).

Molle W. et al. in *J Immunol* 1997, 159, 3555.

Morel, J. B. and Dangle, J.L., *Cell Death Differ* 1997, 4, 67 1.

Ohnishi et al., "A furin–defective cell line is able to process correctly the gp160 of human immunodeficiency virus type I", J Virol, 68(6):4075–99 (1994).

Okumura et al., "The extracellular processing of HIV–1 envelope glycoprotein gp160 by human plasmin", FEBS Lett, 442(1):39–42 (1998).

Pellegrini A, Thomas U, Franchini M, Stockli M, Klauser S, Hunziker P, von Fellenberg R. Identification of an aprotinin antiviral domain. FEBS Lett May 16, 1994;344(2–3):261–5.

Schwartz, et al., "Antiviral activity of the proteasome on incoming human immunodeficiency virus type I", J Virol, 72(5):3845–50) (1998).

Sichko ZhV, Koslova OL. Experience in treating herpetic infection with trypsin [Article in Russian]. Vrach Delo Mar. 1991;86–9.

Szeghy G, Kenyeres B. On the therapy of herpes simplex keratitis with heparin and trypsin. [Article in German] Klin Monatsbl Augenheilkd 1968; 153(6):827–30.

Cilberto et al., 1985, Cell, 41:531–540.

Dery O. and Bunnett, N.W. Biochem Soc Trans 1999, 27, 246–254.

Altieri, D.C. J Leukoc Biol 1995, 58, 120–127.

Dery, O. et al. Am J Physiol 1998, 274, C1429–C1452.

Patel R. P., et al. in Biochim Biophys Acta 1999, 1411, 385–400.

Lowenstein, C. J. and Snyder, S. H. in Cell 1992, 70, 705–707.

Beck, K.F. et al. in J Exp Biol 1999, 202, 645–53.

Kirkeboen, K.A. and Strand, O.A. in Acta Anaesthesiol Scand 1999, 43, 275.

Wood, E. R. et al. in Biochem Biophys Res Commun 1993, 191, 767–74.

Lowenstein C. J. et al. in Proc. Natl. Acad. Sci. USA, 1993, 90, 9730.

Nathan, C. in FASEB J. 1992, 6, 3501.

Rehman, A. et al. in Br J Pharmacol, 1997, 122, 1702.

Pryor, W. A. et al., in Chem Biol Interact 1985, 54, 171.

Van Molle W. et al. in J Immunol 1997, 159, 3555.

Bratt, J. and Palmblad, J. in J Immunol 1997, 159, 812.

Ding, A. et al., in J. Immunol. 1990, 145, 940.

Heck, D. E. et al., in J. Biol. Chem. 1990, 267, 21277.

McCall, T.B. et al., in Biochem. Biophys. Res. Commun. 1992, 186, 680.

Punjabi, C. J. et al., in J. Immunol. 1992, 149, 2179.

Goureau, O. et al., in Proc. Natl. Acad. Sci. U.S.A. 1993, 90, 4276.

Schini et al. in Circ Res 1994, 74, 24.

Meki, A. R. et al. in Toxicon 1998, 36, 18519.

Popko B. and Baerwald, K. D. in Neurochem Res 1999, 24, 331.

Smith, M. E. in Neurochem Res 1999, 24, 261.

Sambrook, Fristsch & Maniatis, Molecular Cloning: A Laboratory Manual, Second Edition 1989, Cold Spring Harbor Laboratory Press, Cold Spring Harbor, N.Y.

Remington's Pharmaceutical Sciences, 1990, p. 1519–1675, Gennaro, A.R., ed., Mack Publishing Company, Easton, PA.

Langer, R., Nature, 1998, 392, 5.

Budavari, Susan (Editor), "The Merck Index", An Encyclopedia of Chemicals, Drugs, and Biologicals; Merck & Co., Inc., 11th edition.

Merrifield, R.B., "Solid Phase Peptide Synthesis. I. The Synthesis of a Tetrapeptide", 1963, J. Am. Chem. Soc., (85):2149.

Animal Cell Culture, R.I. Freshney, ed. 1986, IRL Press, Oxford.

Scharpe et al., "Protease and their inhibitors: today and tomorrow", 1991, Biochimie, 73(1):121–126.

Kido et al., "A novel membrane–bound serine esterase in human T4+ lymphocytes immunologically reactive with antibody inhibiting syncytia induced by HIV–1. Purification and characterization", J Biol Chem., 1990, 265(35):21979–85.

Brinkman et al., "Inhibition of tryptase TL2 from human T4+ lymphocytes and inhibition of HIV–1 replication of H9 cells by recombinant aprotinin and bikunin homologues", 1997, J. Protein Chem., 16(6)(:651–660.

Auerswald et al., "K15R M52E) aprotinin is a weak Kunitz-type inhibitor of HIV–1 replication in H9 cells" Biomed Biochim Acta, 1991, 50(4–6):697–700.

Kamoshita et al., "Calcium requirement and inhibitor spectrum for intracellular HIV type 1 gp160 processing in cultured HeLa cells and CD4+ lymphocytes: similarity to those of viral envelope glycoprotein maturase", J Biochem. Tokyo, 1995, 117(6):1244–53.

Koito et al., "A neutralizing epitope of human immunodeficiency virus type 1 has homologous amino acid sequence with the active site of inter–alpha–trypsin inhibitor", 1989, Int Immunol, 1(6):613–8.

McNeely et al., "Secretory leukocyte protease inhibitor: a human saliva protein exhibiting anti–human immunodeficiency virus 1 activity in vitro", 1995, J Clin Invest, 96(1):456–64.

Hallenberger et al., "Inhibition of furin–mediated cleavage activation of HIV–1 glycoprotein gp160", 1992, Nature, 360(6402):358–61.

Vollenweider, et al., "Comparative cellular processing of the human immunodeficiency virus (HIV–1) envelope glycoprotein gp160 by the mammalian subtilisin/kexin–like convertases", 1996, Biochem. J.;314 (Pt2):521–32.

Anderson et al., "Inhibition of HIV–1 gp160–dependent membrane fusion by a furin–directed alpha 1–antitrypsin variant", 1993, J Biol Chem, 268(33):24887–91.

Decroly, et al., "Identification of the paired basic convertases implicated in HIV gp160 processing based on in vitro assays and expression in CD4(+) cell lines", 1996, J Biol Chem, 271(48):30442–50.

Moulard, et al., "Kex2p: a model for cellular endoprotease processing human immunodeficiency virus type 1 envelope glycoprotein precursor", Eur J Biochem, 1994, 225(2):565–72.

Avril, et al., "Identification of the U–937 membrane–associated proteinase interacting with the V3 loop of HIV–1 gp120 as cathespin G", FEBS Lett, 1994, 345(1):81–6.

Harvima et al., "Separation and partial characterization of proteinases with substrate specificity for basic amino acids from human MOLT–4 T lymphocytes: identification of those inhibited by variable–loop–V3 peptides of HIV–1 (human immunodeficiency virus–1) envelope glycoprotein", 1993, Biochem J, 292 (Pt 3):711–8.

Bourinbaiar, et al., "Acrosin inhibitor, 4'–acetamidophenyl 4–guanidinobenzoate, an experimental vaginal contraceptive and anti–HIV activity", Contraception, 1995, 51(5):319–22.

Bristow, et al., "Inhibition of HIV–1 by modification of a host membrane protease", 1995, Int Immunol, 7(2):239–49.

Bukrinskaia et al., "Inhibition of HIV reproduction in cultured cells using proteolysis inhibitors", 1989, *Vopr Virusol*, 34(1):53–5.

Bourinbair, et al., "Effect of serine protease inhibitor, N–alpha–tosyl–L–lysyl–chloromethyl ketone (TLCK), on cell–mediated and cell–free HIV–1 spread", *Cell Immunol*, 1994, 155(1):230–6.

Turpin et al., "Human immunodeficiency virus type–1 (HIV–1) replication is unaffected by human secretory leukocyte protease inhibitor", 1996, *Antiviral Res*, 29(2–3):269–77.

Kennedy et al., "Submandibular salivary proteases: lack of a role in anti–HIV activity", 1998, *J Dent Res*, 77(7):1515–9.

Premack, B.A. et al., "Chemokine Receptors: Gateways to Inflammation and Infection", 1996, *Nature Medicine* 2:1174–1178.

Zhirnov O.P. et al., "Antiviral activity of proteinase inhibitors in cultured cells infected with alpha–viruses", *Mol Gen Mikrobiol Virusol*, 1985, (12):30–6.

Chesnokova N.B. et al., "Antiproteases in herpetic keratitis", *Metab Pediatr Syst Ophthalmol*, 1986;9(1):593–6.

Adelman S.F. et al., "Protease inhibitors suppress fibrinolytic activity of herpesvirus–transformed cells", *J Gen Virol*, 1982, 60(Pt 1):15–24.

Chesnokova N.B. et al., "Main proteolytic inhibitors in ocular herpes", *Vopr Med Khim*, 1981, 27(5):663–5.

Sharpstone D. et al., "Faecal alpha 1 antitrypsin as a marker of gastrointestinal disease in HIV antibody positive individuals", *Gut*, 1996, 38(2):206–10.

Patel et al., "The Role of Protease Drug During Apoptosis", 1996, *FASEB J*, 10(5):587–597.

Estaquier J., "Fas–mediated apoptosis of CD4+ and CD8+ T cells from human immunodeficiency virus–infected persons: differential in vitro preventive effect of cytokines and protease antagonists", 1996, *Blood*, 15;87(12):4959–66.

Shimizu, T. et al., "DNA Fragmentation induced by Protease Activation in P53–null Human Leukemia HL60 Cells Undergoing Apoptosis Following Treatment with the Topoisomerase I Inhibitor Camptothecin: Cell–Free System Studies", 1996, *Exp Cell Res*, 1:226(2):292–301.

Glynn et al., "Apoptosis induced by HIV Infection in H9 T Cells is Blocked by ICE–Family Protease Inhibition but not by a FAS(CD95) Antagonist", 1996, *J. Immunol*, 1; 157(7):2754–2758.

Ooka, T., et al., "Protective effects of human uninary trypsin inhibitor against trypsin–induced relaxation in rat aorta", *Crit care Med*, 1996, 24(11): 1903–1907.

Novradovsky, A., et al., "Endothelial Nitric Oxide Synthase as a Potential Susceptibility Gene in the Pathogenesis of Emphysema in alpha1–Antytrypsin Dieficiency", 1999, *Am J Respir Cell Mol Biol*, 1;20(3):441–447.

Cordiali Fei et al., "Behavior of several 'progression markers' during the HIV–Ab seroconversion period. Comparison with later stages", 1992, *J Biol Regul Homeost Agents*, 6(2):57–64).

Lima et al., "Mucosal injury and disruption of intestinal barrier function in HIV–infected individuals with and without diarrhea and cryptosporidiosis in northeast Brazil", 1997, *Am J Gastroenterol*, 92(10):1861–6.

Banfi et al., "Tumor–associated trypsin inhibitor in induced and acquired immunodeficiency. Studies on transplanted and HIV–infected patients", 1991, *Scand J Clin Lab Invest 51*, Suppl, 207:55–8.

Deam et al., "Alpha 1–antitrypsin phenotypes in homosexual men", 1989, Pathology, 21(2):91–2.

Pezzilli et al., "Serum pancreatic enzymes in HIV–seropositive patients", *Dig Dis Sci*, 1992, 37(2):286–8.

Tang et al., "Inactivation of HIV–1 by trypsin and its use in demonstrating specific virus infection of cells", 1991, J Virol Methods, 33(1–2):39–46.

Glozman, "Immunologic functions of enzyme therapy of patients with orchiepidymitis", 1990, *Antibiot. Khimioter*, 35(7):50–52.

Franzusoff, et al., "Biochemical and genetic definition of the cellular protease required for HIV–1 gp160 processing", 1995, *J Biol Chem*, 270(7):3154–9).

Gu et al., "Furin is important but not essential for the proteolytic maturation of gp160 of HIV–1", *FEBS Lett.* 1995, 365(1):95–7.

Bukrinskaia A.G., "Suppression of rotavirus SA–11 reproduction by protease inhibitors in cell culture", *Vopr Virusol*, 1987, 32(1):71–4.

* cited by examiner

EFFECT OF AAT ON CMV PRODUCTION
(N=1, DUPLICATE)

AAT: EFFECT ON HSV-1 INFECTION (N=2)
*** P<0.001 COMPARED TO CONTROL

INHIBITORS OF SERINE PROTEASE ACTIVITY, METHODS AND COMPOSITIONS FOR TREATMENT OF NITRIC-OXIDE-INDUCED CLINICAL CONDITIONS

This application claims priority to U.S. Provisional Application No. 60/123,167 filed Mar. 5, 1999 and U.S. Provisional Application No. 60/156,523 filed Sep. 29, 1999 both of which are hereby incorporated by reference.

1. FIELD OF THE INVENTION

The present invention relates to compositions and methods for inhibition of nitric oxide (NO), and to therapeutic treatment of diseases or disorders that involve inappropriate or detrimental NO activity. Thus, the invention relates to modulation of cellular activities, including macrophage activity, endothelial cell function, and the like. The present invention also relates to substances exhibiting inhibitory activity toward nitric oxide-associated diseases, which are facilitated by serine protease activity. More particularly, the inhibitory compounds comprise naturally occurring and man-made serine protease inhibitors and antagonists.

2. BACKGROUND OF THE INVENTION

2.1. Serine Proteases

Serine proteases serve an important role in human physiology by mediating the activation of vital functions. In addition to their normal physiological function, serine proteases have been implicated in a number of pathological conditions in humans. Serine proteases are characterized by a catalytic triad consisting of aspartic acid, histidine and serine at the active site.

The naturally occurring serine protease inhibitors are usually, but not always, polypeptides and proteins which have been classified into families primarily on the basis of the disulfide bonding pattern and the sequence homology of the reactive site. Serine protease inhibitors, including the group known as serpins, have been found in microbes, in the tissues and fluids of plants, animals, insects and other organisms. Protease inhibitor activities were first discovered in human plasma by Fermi and Pemossi in 1894. At least nine separate, well-characterized proteins are now identified, which share the ability to inhibit the activity of various proteases. Several of the inhibitors have been grouped together, namely $\alpha_1$-proteinase inhibitor, antithrombin III, antichymotrypsin, C1-inhibitor, and $\alpha_2$-antiplasmin, which are directed against various serine proteases, i.e., leukocyte elastase, thrombin, cathepsin G, chymotrypsin, plasminogen activators, and plasmin. These inhibitors are members of the $\alpha_1$-proteinase inhibitor class. The protein $\alpha_2$-macroglobulin inhibits members of all four catalytic classes: serine, cysteine, aspartic, and metalloproteases. However, other types of protease inhibitors are class specific. For example, the $\alpha_1$-proteinase inhibitor (also known as ($\alpha_1$-antitrypsin or AAT) and inter-alpha-trypsin inhibitor inhibit only serine proteases, $\alpha_1$-cysteine protease inhibitor inhibits cysteine proteases, and $\alpha_1$-anticollagenase inhibits collagenolytic enzymes of the metalloenzyme class.

Human neutrophil elastase (NE) is a proteolytic enzyme secreted by polymorphonuclear leukocytes in response to a variety of inflammatory stimuli. The degradative capacity of NE, under normal circumstances, is modulated by relatively high plasma concentrations of $\alpha_1$-antitrypsin. However, stimulated neutrophils produce a burst of active oxygen metabolites, some of which (hypochlorous acid for example) are capable of oxidizing a critical methionine residue in $\alpha_1$-antitrypsin. Oxidized $\alpha_1$-antitrypsin has been shown to have a limited potency as a NE inhibitor and it has been proposed that alteration of this protease/antiprotease balance permits NE to perform its degradative functions in localized and controlled environments.

$\alpha_1$-Antitrypsin is a glycoprotein of MW 51,000 with 417 amino acids and 3 oligosaccharide side chains. Human $\alpha_1$-antitrypsin was named anti-trypsin because of its initially discovered ability to inactivate pancreatic trypsin. Human $\alpha_1$-antitrypsin is a single polypeptide chain with no internal disulfide bonds and only a single cysteine residue normally intermolecularly disulfide-linked to either cysteine or glutathione. The reactive site of $\alpha_1$-antitrypsin contains a methionine residue, which is labile to oxidation upon exposure to tobacco smoke or other oxidizing pollutants. Such oxidation reduces the biological activity of $\alpha_1$-antitrypsin; therefore substitution of another amino acid at that position, i.e. alanine, valine, glycine, phenylalanine, arginine or lysine, produces a form of $\alpha_1$-antitrypsin which is more stable. $\alpha_1$-Antitrypsin can be represented by the following formula:

```
      1        0 1        0 1        0 1        0 1         0

MPSSVSWGIL LAGLCCLVPV SLAEDPQGDA AQKTDTSHHD QDHPTFNKIT

PNLAEFAFSL YRQLAHQSNS TNIFFSPVSI ATAFAMLSLG TKADTHDEIL  100

EGLNFNLTEI PEAQIHEGFQ ELLRTLNQPD SQLQLTTGNG LFLSEGLKLV

DKFLEDVKKL YHSEAFTVNF GDHEEAKKQI NDYVEKGTQG KIVDLVKELD  200

RDTVFALVNY IFFKGKWERP FEVKDTEDED FHVDQVTTVK VPMMKRLGMF

NIQHCKKLSS WVLLMKYLGN ATAIFFLPDE GKLQHLENEL THDIITKFLE  300

NEDRRSASLH LPKLSITGTY DLKSVLGQLG ITKVFSNGAD LSGVTEEAPL

KLSKAVHKAV LTIDEKGTEA AGAMFLEAIP MSIPPEVKFN KPFVFLMIEQ  400

NTKSPLFMGK VVNPTQK                                     417
```

Ciliberto, et al. in *Cell* 1985, 41, 531–540. The critical amino acid sequence near the carboxyterminal end of $\alpha_1$-antitrypsin is shown in bold and is pertinent to this invention.

The C-terminus of human $\alpha_1$-antitrypsin is homologous to antithrombin (ATIII), antichymotrypsin (ACT), C1-inhibitor, tPA-inhibitor, mouse anti-trypsin, mouse contrapsin, barley protein Z, and ovalbumin. The normal plasma concentration of ATT ranges from 1.3 to 3.5 mg/ml although it can behave as an acute phase reactant and increases 3–4-fold during host response to inflammation and/or tissue injury such as with pregnancy, acute infection, and tumors. It easily diffuses into tissue spaces and forms a 1:1 complex with a target protease, principally neutrophil elastase. Other enzymes such as trypsin, chymotrypsin, cathepsin G, plasmin, thrombin, tissue kallikrein, and factor Xa can also serve as substrates. The enzyme/inhibitor complex is then removed from circulation by binding to serpin-enzyme complex (SEC) receptor and catabolized by the liver and spleen. Humans with circulating levels of $\alpha_1$-antitrypsin less than 15% of normal are susceptible to the development of lung disease, e.g., familial emphysema, at an early age. Familial emphysema is associated with low ratios of $\alpha_1$-antitrypsin to serine proteases, particularly elastase. Therefore, it appears that this inhibitor represents an important part of the defense mechanism against attack by serine proteases.

$\alpha_1$-Antitrypsin is one of few naturally occurring mammalian serine protease inhibitors currently approved for the clinical therapy of protease imbalance. Therapeutic $\alpha_1$-antitrypsin has been commercially available since the mid 80s and is prepared by various purification methods (see for example Bollen et al., U.S. Pat. No. 4,629,567; Thompson et al., U.S. Pat. Nos. 4,760,130; 5,616,693; WO 98/56821). Prolastin is a trademark for a purified variant of $\alpha_1$-antitrypsin and is currently sold by Bayer Company (U.S. Pat. No. 5,610,285 Lebing et al., Mar. 11, 1997). Recombinant unmodified and mutant variants of $\alpha_1$-antitrypsin produced by genetic engineering methods are also known (U.S. Pat. No. 4,711,848); methods of use are also known, e.g., ($\alpha_1$-antitrypsin gene therapy/delivery (U.S. Pat. No. 5,399,346 to French Anderson et al.).

The two known cellular mechanisms of action of serine proteases are by direct degradative effects and by activation of G-protein-coupled proteinase-activated receptors (PARs). The PAR is activated by the binding of the protease followed by hydrolysis of specific peptide bonds, with the result that the new N-terminal sequences stimulate the receptor. The consequences of PAR activation depend on the PAR type that is stimulated and on the cell or tissue affected and may include activation of phospholipase C$\beta$, activation of protein kinase C and inhibition of adenylate kinase (Dery, O. and Bunnett, N. W. *Biochem Soc Trans* 1999, 27,246–254; Altieri, D. C. *J. Leukoc Biol* 1995, 58, 120–127; Dery, O. et al. *Am J. Physiol* 1998, 274, C1429–C1452).

2.2. Nitric Oxide (NO)

Nitric oxide (NO), also known as endothelium-derived relaxing factor (EDRF), is a potent vasodilator, oxidant, and neurotransmitter produced by many different types of cells and tissues, such as endothelium, macrophages and neuronal cells reviewed by Patel R. P., et al. in *Biochim Biophys Acta* 1999, 1411, 385–400; Lowenstein, C. J. and Snyder, S. H. in *Cell* 1992, 70, 705–707; Nathan, C. in *FASEB J.* 1992, 6, 3051.

A presently dominant theory based on DNA analyses holds that the NO synthase enzymes (NOS) exist in at least three isoforms, namely, neuronal constitutive NOS (N-cNOS) which is present constitutively in neurons, endothelial constitutive NOS (E-cNOS) which is present constitutively in endothelial cells, and inducible NOS (iNOS) which is expressed following stimulation by cytokines and lipopolysaccharides in macrophages and many other cells. (see Beck, K. F. et al. in *J. Exp Biol* 1999, 202, 645–53; Kirkeboen, K. A. and Strand, O. A. in *Acta Anaesthesiol Scand* 1999, 43, 275; Wood, E. R. et al. in *Biochem Biophys Res Commun* 1993, 191, 767–74; Lowenstein C. J. et al. in *Proc. Natl. Acad. Sci. USA,* 1993, 90, 9730). Among these three isoforms, N-cNOS and E-cNOS are calcium-dependent whereas iNOS is calcium-independent (Nathan, C. in *FASEB J.* 1992, 6, 3051). NO synthesized by nitric oxide synthase from arginine and oxygen is also an important signal transducing molecule in various cell types (Nathan, 1992, supra). In macrophages NO has assumed, under certain situations, the role of a cytotoxic agent—a reactive nitrogen intermediate that is lethal to cancer cells and microorganisms. The release of nitric oxide is also involved in other acute and chronic inflammatory diseases. These diseases include but are not limited to diseases such as, for example, acute and chronic infections (viral, bacterial and fungal), acute and chronic bronchitis, sinusitis, and upper respiratory infections, including the common cold; acute and chronic gastroenteritis and colitis; acute and chronic cystitis, and urethritis; acute and chronic dermatitis; acute and chronic conjunctivitis; acute and chronic serositis (pericarditis, peritonitis, synovitis, pleuritis and tendinitis); uremic pericarditis; acute and chronic cholecystitis; acute and chronic vaginitis; drug reactions; insect bites; burns and sunburn.

Released NO combines very rapidly with superoxide to form peroxynitrite (ONOO$^-$), a reactive tissue damaging nitrogen species thought to be involved in the pathology of several chronic diseases. Peroxynitrite nitrates tyrosine residues and inactivates $\alpha_1$-antitrypsin (Rehman, A. et al. in *Br J Pharmacol,* 1997, 122, 1702). This mechanism is postulated to be responsible for $\alpha_1$-antitrypsin inactivation by cigarette smoke (Pryor, W. A. et al., in *Chem Biol Interact* 1985, 54, 171). Nitric oxide inhibits iron-containing enzymes important in respiration and DNA synthesis. Peroxynitrite decomposes to the reactive NO$_2$ and hydroxyl radicals, and NO stimulates ADP-ribosylation of various proteins including glyceraldehyde-3-phosphate dehydrogenase, with consequent inactivation.

Van Molle and colleagues have shown that the acute phase protein $\alpha_1$-antitrypsin inhibits the cellular lethality induced by tumor necrosis factor (TNF) both in normal mice and in mice sensitized with galactosamine but similar apoptosis of hepatocytes induced by anti-Fas remained unaffected. Molle W. et al. in *J Immunol* 1997, 159, 3555. However, $\alpha_1$-antitrypsin did not affect the induction by TNF of NO Van Molle, ibid. In contrast, Bratt and colleagues have shown that TNF injury was not prevented by $\alpha_1$-antitrypsin (Bratt, J. and Palmblad, J. in *J Immunol* 1997, 159, 812).

Many proteins are reported to modulate NO production. Macrophage deactivating factor and TGF-$\beta$ partially blocked NO release by macrophages activated with $\gamma$-interferon ($\gamma$-IFN or IFN-$\gamma$) and TGF-$\alpha$ (transforming growth factor-$\alpha$), but not when activated by $\gamma$-IFN and lipopolysaccharide (LPS or endotoxin) (Ding, A. et al., in *J. Immunol.* 1990, 145, 940). Epidermal growth factor can suppress both NO and H$_2$O$_2$ production by keratinocytes (Heck, D. E. et al., in *J. Biol. Chem.* 1990, 267, 21277). Incubation of LPS-activated peritoneal neutrophils with IL-8 blocks both the release of NO and NOS induction at the transcriptional level (McCall, T. B. et al., in *Biochem. Biophys. Res. Commun.* 1992, 186, 680).

TGF-$\beta_1$ and 12-O-tetradecanoylphorbol-13-acetate (i.e., phorbol myristyl acetate or PMA) inhibit LPS and $\gamma$-IFN-induced NO synthesis in mouse bone marrow cells (Punjabi, C. J. et al., in *J. Immunol.* 1992, 149, 2179). In contrast, in bovine pigmented retinal epithelial cells TGF-$\beta$ increases the NO production, as measured by nitrite, attributable to treatment with LPS and $\gamma$-IFN. In this system both fibroblast growth factor (FGF)-1 and FGF-2 inhibit nitrite production, likely by inhibiting the induction of NOS mRNA at the transcriptional level (Goureau, O. et al., in *Proc. Natl. Acad. Sci. U.S.A.* 1993, 90, 4276). Insulin-like growth factor 1 reduces the amount of NO produced by the action of IL-$1_{62}$ on vascular smooth muscle cells (Schini et al. in *Circ Res* 1994, 74, 24). The fact that so many agents can modulate NO activity by increasing or inhibiting NO production suggests that NO production may be important in many different contexts.

The overproduction in the body of nitric oxide (NO) and/or peroxynitrite (ONOO$^-$) has been suggested by some to be a contributing factor to diseases that are immune-mediated and/or inflammatory. In a clinical study the levels of IL-6, IL-$1_\beta$, NO and $\alpha_1$-antitrypsin were shown to be involved in the pathogenesis of scorpion envenomation and correlated with the severity of envenomation (Meki, A. R. et al. in Toxicon 1998, 36, 18519). An extensively used model system to study multiple sclerosis, an example of a disease treated by the present invention, is experimental allergic encephalomyelitis (EAE) in rats and mice. (Popko B. and Baerwald, K. D. in *Neurochem Res* 1999, 24, 331; Smith, M. E. in *Neurochem Res* 1999, 24, 261).

Thus, the prior art taught that NO metabolites inactivate $\alpha_1$-antitrypsin. Also taught was that in certain clinical situations NO levels tended to rise concomitantly along with increase in $\alpha_1$-antitrypsin levels, although the AAT activity may have been reduced. However, the prior art failed to recognize that $\alpha_1$-antitrypsin might in fact prevent NO synthesis. The present inventor discovered that therapeutic and physiological levels of $\alpha_1$-antitrypsin can efficiently block γ-IFN- and LPS-induced NO synthesis. This invention addresses a long-felt need for safe and effective amelioration of many diseases related to nitric oxide-caused damage.

3. SUMMARY OF THE INVENTION

The present invention is directed to a method for treating a disease or disorder involving an excess activity of nitric oxide (NO) in an animal subject. The method of the invention comprises administering a therapeutically effective amount of an agent that reduces NO levels, to an animal subject suspected of having a disease or disorder involving excess nitric oxide. In a preferred embodiment the agent can be $\alpha_1$-antitrypsin. In addition, peptides of interest are homologous and analogous peptides. While homologues are natural peptides with sequence homology, analogues will be peptidyl derivatives, e.g., aldehyde or ketone derivatives of such peptides. Typical examples of analogues are TLCK or TPCK. Without limiting to $\alpha_1$-antitrypsin and peptide derivatives of $\alpha_1$-antitrypsin, compounds like oxadiazole, thiadiazole, CE-2072, UT-77, and triazole peptoids are preferred. The agent that reduces NO levels can also be an $\alpha_1$-antitrypsin-like agent, an inhibitor of elastase, or an inhibitor of proteinase-3. The $\alpha_1$-antitrypsin-like agent can include, but is not limited to, small organic molecules including naturally-occurring, synthetic, and biosynthetic molecules, small inorganic molecules including naturally-occurring and synthetic molecules, natural products including those produced by plants and fungi, peptides, variants of $\alpha_1$-antitrypsin, chemically modified peptides, and proteins. An $\alpha_1$-antitrypsin-like agent has the capability of inhibiting the proteolytic activity of trypsin, elastase, kallikrein, and/or other serine proteases.

A general method of treating a mammal suffering from a pathological condition that is mediated by endogenous serine protease or serine protease-like activity is contemplated as well, which comprises administering a therapeutically effective amount of a substance exhibiting mammalian $\alpha_1$-antitrypsin or $\alpha_1$-antitrypsin-like activity. The pathological condition can be precipitated at least in part by abnormal nitric oxide levels.

Also a method is provided of inhibiting bacterial colonization in a host, which comprises administering to a mammal susceptible to bacterial colonization an effective amount of a substance exhibiting mammalian $\alpha_1$-antitrypsin or $\alpha_1$-antitrypsin-like activity. Without limiting to $\alpha_1$-antitrypsin, the substance may be a compound that inhibits proteinase-3, cathepsin G, or elastase.

Also contemplated is a method of preventing a deficiency of functional endogenous $\alpha_1$-antitrypsin levels in a patient susceptible to an infection that is mediated by endogenous host serine protease or serine protease-like activity, by treating with a pharmaceutical composition in a pharmaceutically acceptable carrier comprising effective amounts of a substance exhibiting mammalian $\alpha_1$-antitrypsin or $\alpha_1$-antitrypsin-like activity. In addition, to reduce ischemia-reperfusion injury associated with administration of thrombolytics, a combination of serine protease inhibitor, and a thrombolytic agent such as tissue plasminogen activator, urokinase, streptokinase, or combinations or complexes thereof can be administered. The pharmaceutical composition can be a peptide or a small molecule, which exhibits $\alpha_1$-antitrypsin or $\alpha_1$-antitrypsin-like activity.

It should be apparent that in addition to these preferred embodiments a method is contemplated which consists of treating an individual having a pathological condition caused, in whole or part, by nitric oxide release. In accordance with this embodiment, a method of inhibiting nitric oxide release is provided wherein the target of the therapy is a cell and one will contact such cell with an effective amount of a compound having $\alpha_1$-antitrypsin activity.

According to the invention, the peptide can be protected or derivitized in various ways, e.g., N-terminal acylation, C-terminal amidation, cyclization, etc. In a specific embodiment, the N-terminus of the peptide is acetylated.

The invention further provides pharmaceutical compositions comprising such agents. In yet a further embodiment of the invention, the pharmaceutical composition also comprises a vasoconstrictor effective to increase blood pressure in an animal.

It is therefore the goal of the present invention, in its broadest aspect, to provide methods of treating diseases dependent on the action of NO and proteases. Accordingly, it should be recognized that this invention is applicable to the control of catalytic activity of serine proteases in any appropriate situation including, but not necessarily limited to, medicine, biology, agriculture, and microbial fermentation.

Accordingly, it is therefore the overall object of the present invention to provide compounds that exhibit inhibitory activity toward serine proteases.

It is an object of the present invention to provide clinically acceptable serine protease inhibitors with recognized utility and exhibiting relatively high activity at relatively low concentrations.

It is yet another object of the invention to provide means of regulating nitric oxide release by compounds having $\alpha_1$-antitrypsin activity.

These and other objects and advantages of the present invention will be recognized by those skilled in the art from the following description and illustrative examples.

4. BRIEF DESCRIPTION OF THE DRAWINGS

5. DETAILED DESCRIPTION OF THE INVENTION

5.1. Standard Methods

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual, Second Edition* 1989, Cold Spring Harbor Laboratory Press, Cold Spring Harbor, N.Y.; *Animal Cell Culture*, R. I. Freshney, ed., 1986).

5.2. Serine Protease Inhibitors

In a particular embodiment of the treatment process, a pharmacologically active dose of a serine protease inhibitor is administered, regardless of whether or not a nitric oxide or peroxynitrite scavenger, an antioxidant, or another anti-iNOS agent is administered.

Inhibition of NO production has many important therapeutic benefits, as described infra. NO production contributes to septic shock, the adverse consequences of ischemia, inflammation including acne, hypotension, cell death and other physiological processes and effects. The cytokines IL-2 and TNF, which have significant potential as therapeutic agents to treat cancer, induce high levels of NO production, resulting in hypotensive shock. This adverse side effect is reversed by administering NO inhibitors with these cytokines. Thus, the functional agents of the invention may be useful as primary or ancillary therapeutic agents for the treatment of these and other NO-mediated diseases or disorders, or effects.

Figure 1:
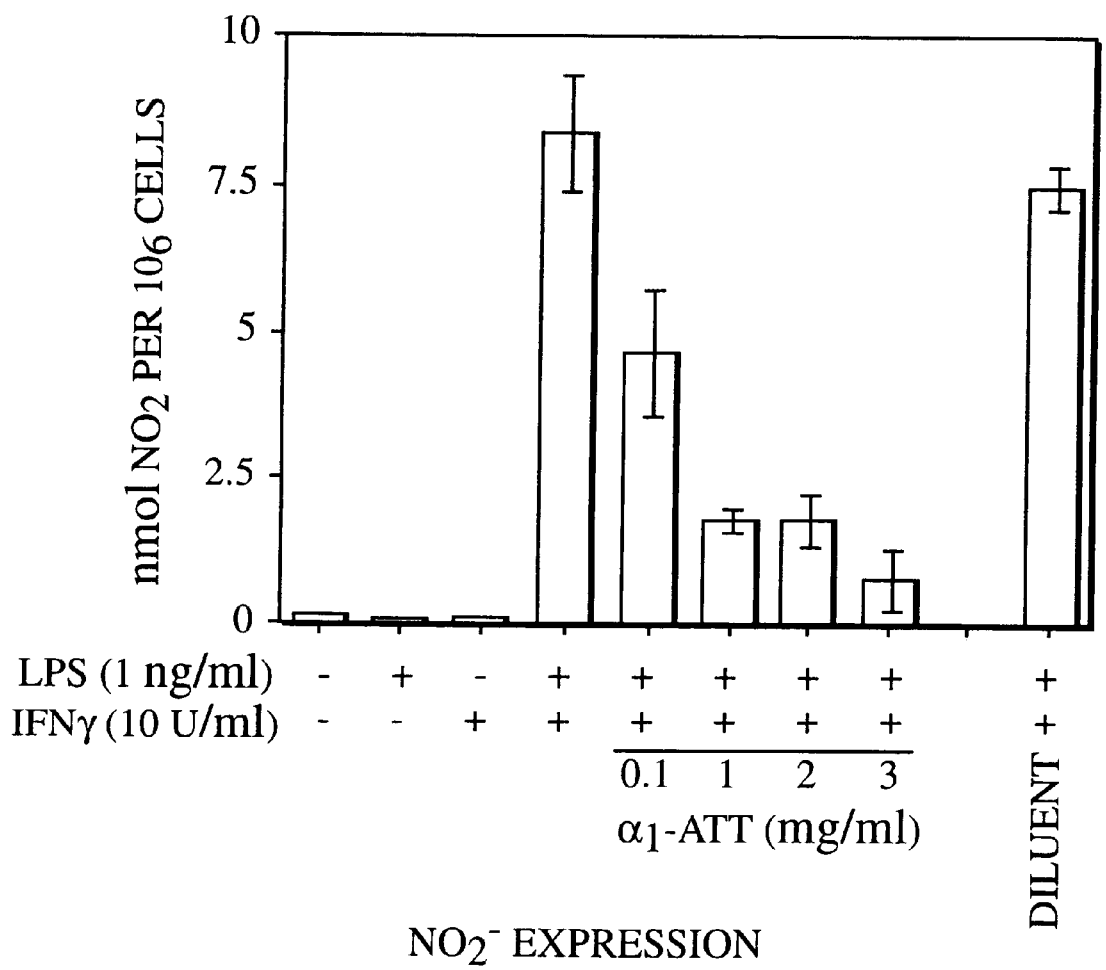
FIG. 1 illustrates the effect of $\alpha_1$-antitrypsin on NO release upon induction with LPS and γ-IFN.

FIG. 1 illustrates a specific embodiment of the invention in which, $\alpha_1$-antitrypsin inhibits NO levels induced by the inflammatory mediators γ-interferon (γ-IFN) and lipopolysaccharide (LPS) in macrophagic cells. Analyses of inducible nitric oxide synthase expression reveal that the inflammatory mediators increase NO levels, and that $\alpha_1$-antitrypsin inhibits the induction.

Figure 2:
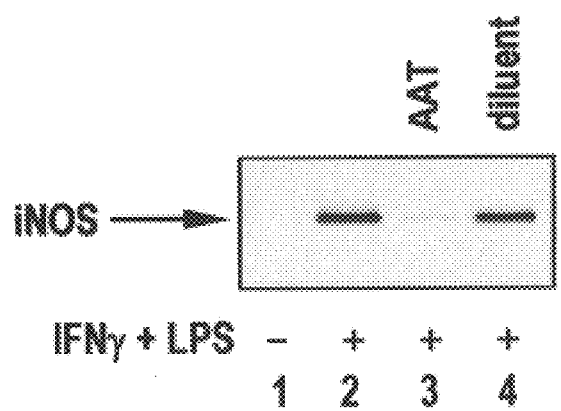
FIG. 2 illustrates the effect of $\alpha_1$-antitrypsin on induction of iNOS protein by LPS and γ-interferon.

FIG. 2 illustrates another specific embodiment of the invention, in which $\alpha_1$-antitrypsin inhibits induction of iNOS protein (one of the enzymes responsible for NO synthesis) induced by the inflammatory mediators γ-interferon (γ-IFN) and lipopolysaccharide (LPS) in macrophagic cells. Western blot analyses of inducible nitric oxide synthase expression reveals that the inflammatory mediators increases iNOS protein levels, and that $\alpha_1$-antitrypsin inhibits the induction.

Figure 3:
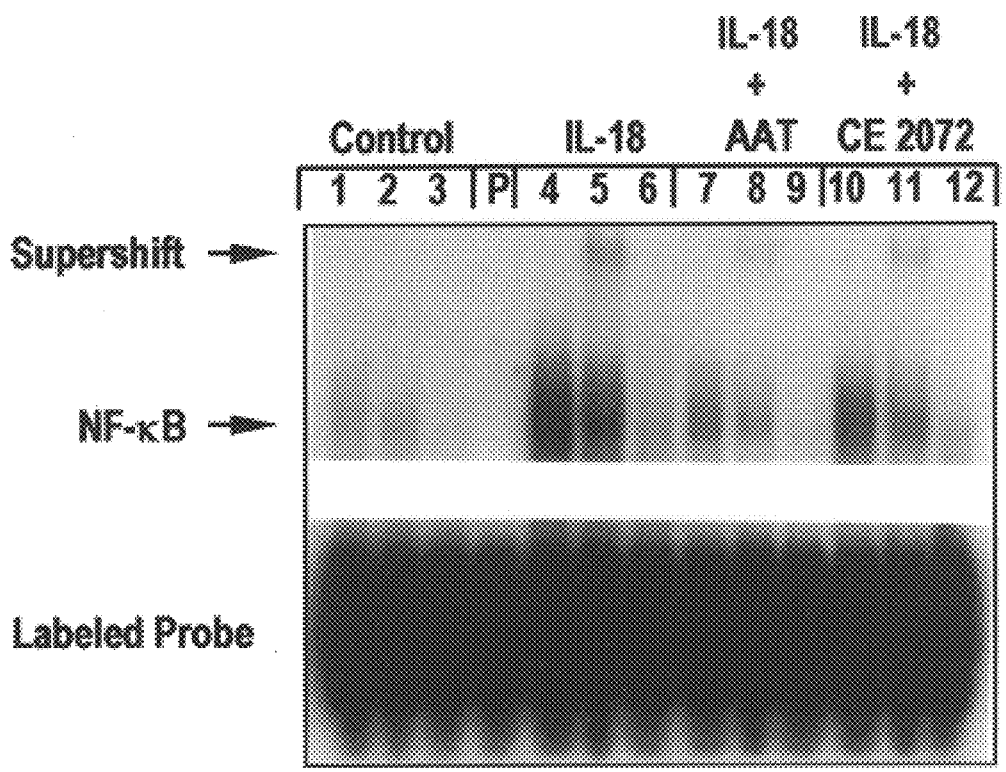
FIG. 3 illustrates an electrophoretic mobility shift assay of NF-κB on gel electrophoresis demonstrating inhibition of NF-κB activation due to the presence of $\alpha_1$-antitrypsin.

FIG. 3 illustrates the electrophoretic mobility shift due to nuclear factor-κB (NF-κB) induced by incubation with interleukin-18 (IL-18). NF-κB is a positive regulator of NOS induction. As illustrated by the figure, both $\alpha_1$-antitrypsin and CE-2072 inhibit the induction of active NF-κB.

Figure 4:
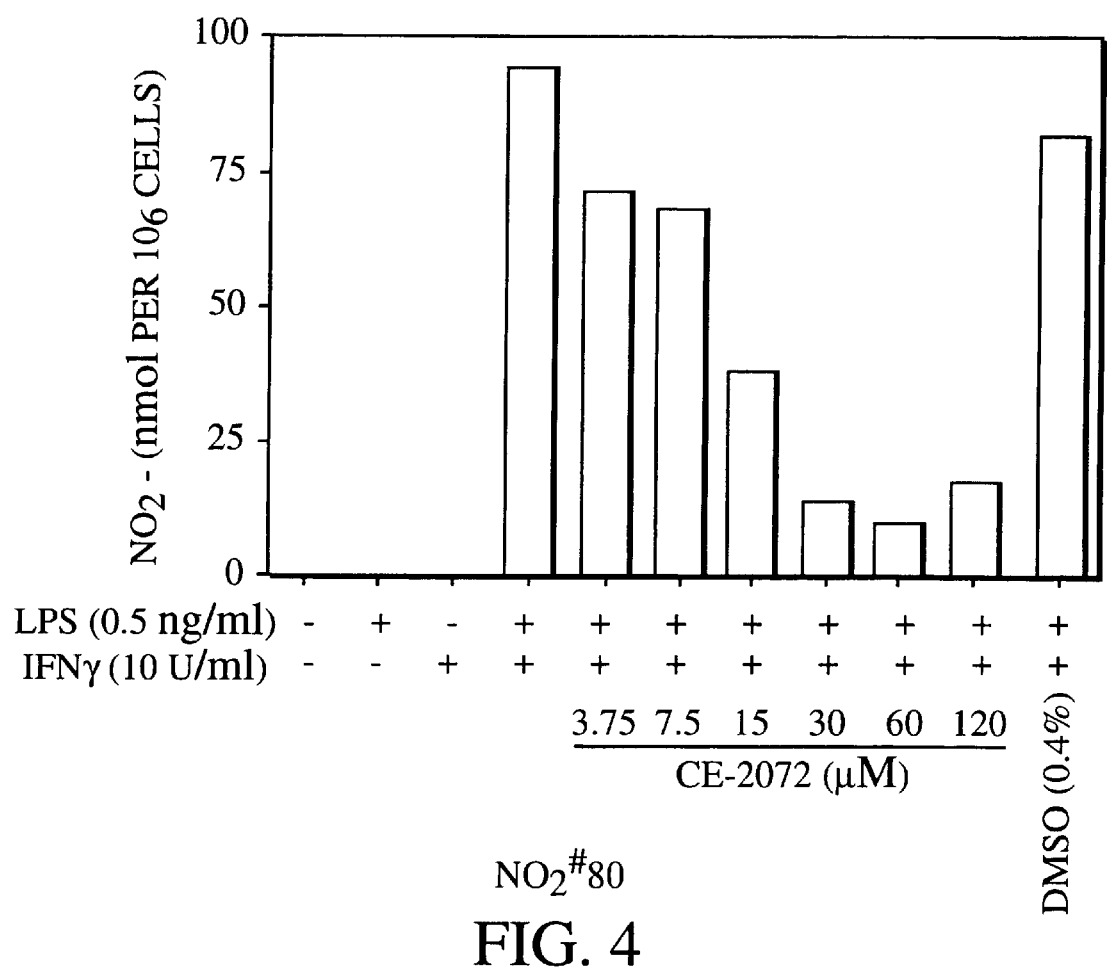
FIG. 4 illustrates the inhibition of elevated NO levels, measured as $NO_2^-$, by CE-2072.

FIG. 4 illustrates yet another specific embodiment of the invention, in which CE-2072 inhibits NO levels resulting from induction of iNOS by IFN-γ and LPS. CE-2072, a peptoid with the structure benzyloxycarbonyl-L-valyl-N-[1-(2-[5-(3-methylbenzyl)-1,3,4-oxadiazolyl] carbonyl)-2-(S)-methylpropyl]-L-prolinamide, is revealed in this figure to be an inhibitor of NO.

Figure 5:
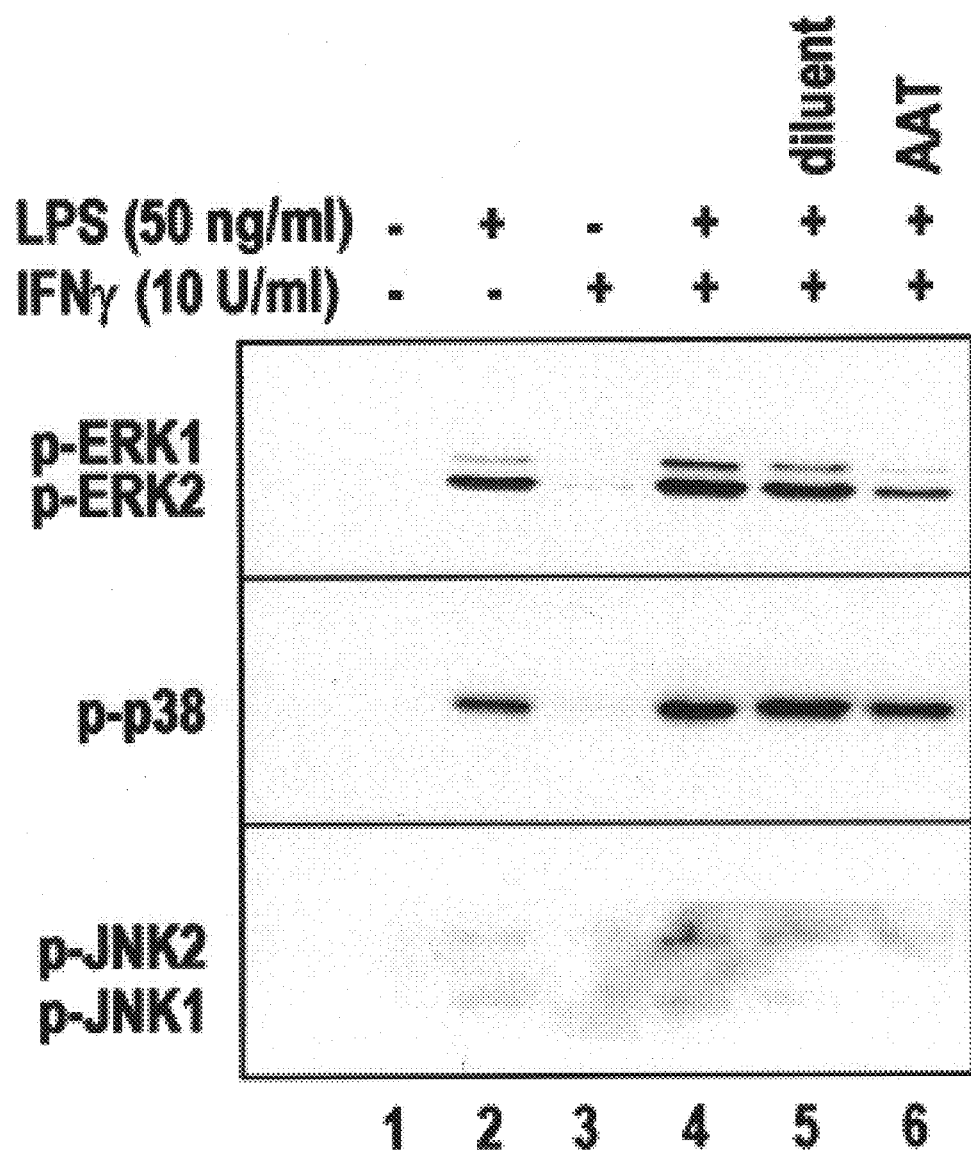
FIG. 5 illustrates the inhibition of p-ERK expression by $\alpha_1$-antitrypsin (AAT).

FIG. 5 illustrates still another embodiment of the invention, in which $\alpha_1$-antitrypsin inhibits the level and/or phosphorylation of p-ERK (phospho-extracellular signal regulated kinase, also termed p42/p44 MAP kinase. The figure is a Western blot (protein blot of SDS-polyacrylamide electrophoresis) of p38 and p-ERK, and an autoradiograph of p-JNK SDS polyacrylamide electrophoresis.

Figure 6:
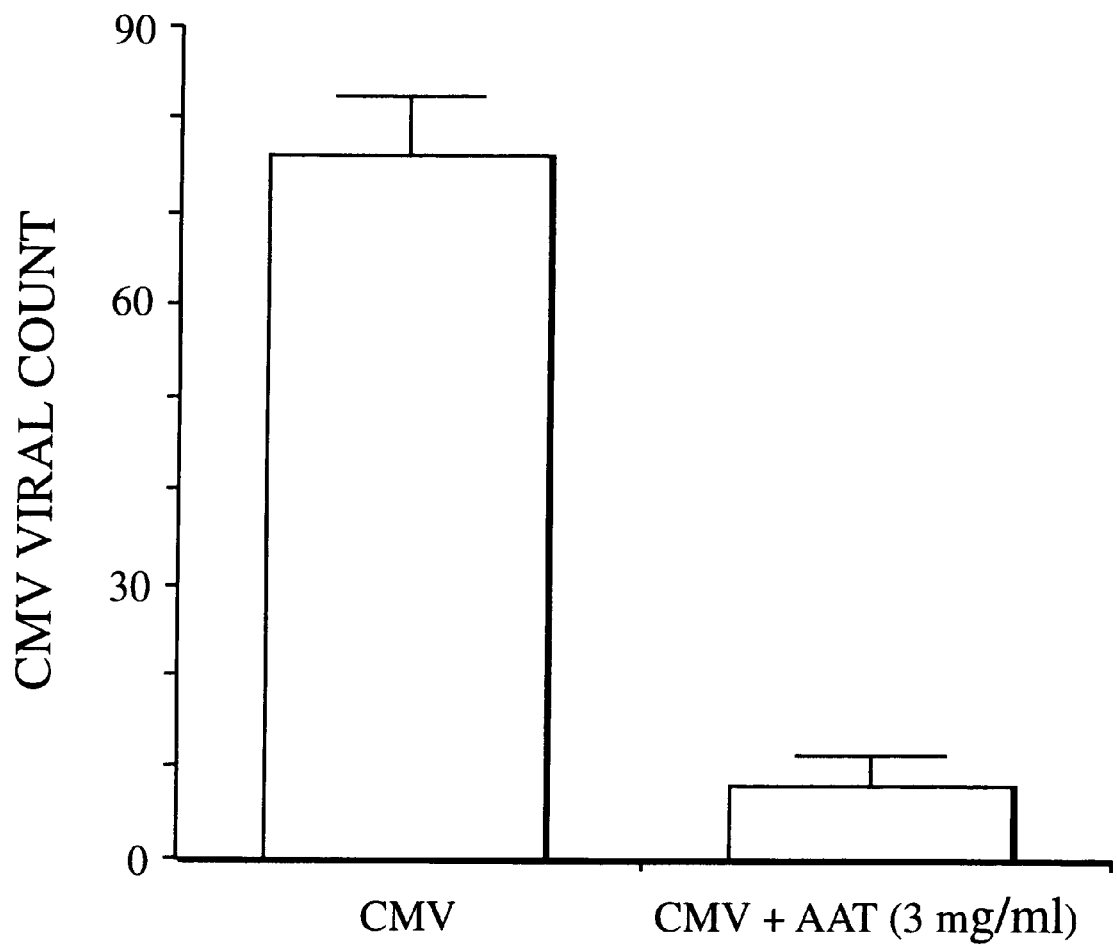
FIG. 6 illustrates the effect of $\alpha_1$-antitrypsin on cytomegalovirus replication.

FIG. 6 illustrates the effect of $\alpha_1$-antitrypsin on replication of cytomegalovirus (CMV). RAW 264.5 macrophages infected with CMV are treated in the absence or presence of $\alpha_1$-antitrypsin, which, as the figure illustrates, blocks CMV replication.

Figure 7:
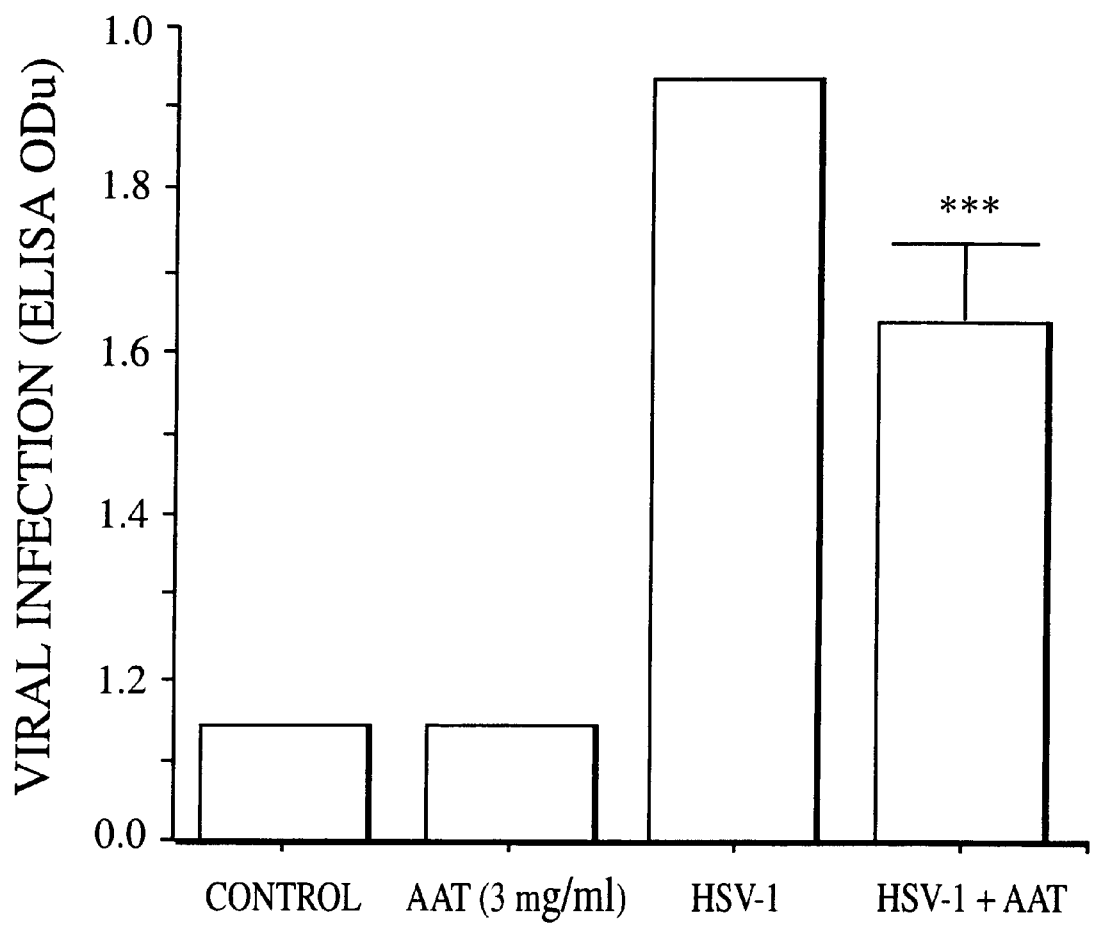
FIG. 7 illustrates the effect of $\alpha_1$-antitrypsin on herpes simplex infection.

FIG. 7 illustrates the effect of $\alpha_1$-antitrypsin on herpes simplex virus (HSV).

Alpha$_1$-antitrypsin inhibits replication of HSV in this system.

It is to be understood that the present invention is not limited to the examples described herein, and other serine proteases known in the art can be used within the limitations of the invention. For example, one skilled in the art can easily adopt inhibitors as described in WO 98/24806, which discloses substituted oxadiazole, thiadiazole and triazole as serine protease inhibitors. U.S. Pat. No. 5,874,585 discloses substituted heterocyclic compounds useful as inhibitors of serine proteases; including: (benzyloxycarbonyl)-L-valyl-N-[1-(3-(5-(3-trifluoromethylbenzyl)-1,2,4-oxadiazolyl) carbonyl)-2-(S)-methylpropyl]-L-prolinamide benzyloxycarbonyl-L-valyl-N-[1-(3-(5-(2-phenylethyl)-1,2,4-oxadiazolyl)carbonyl)-2-(S)-methylpropyl]-L-prolinamide; (benzyloxycarbonyl)-L-valyl-N-[1-(3-(5-(2-methoxybenzyl)-1,2,4-oxadiazolyl)carbonyl)-2-(S)-methylpropyl]-L-prolinamide; (benzyloxycarbonyl)-L-valyl-N-[1-(3-(5-(trifluoromethyl)-1,2,4-oxadiazolyl) carbonyl)-2-(S)-methylpropyl]-L-prolinamide; (benzyloxycarbonyl)-L-valyl-N-[1-(3-(5-(methyl)-1,2,4-oxadiazolyl)carbonyl)-2-(S)-Methylpropyl]-L-Prolinamide; (Benzyloxycarbonyl)-L-Valyl-N-[1-(3-(5-(difluoromethyl)-1,2,4-oxadiazolyl) carbonyl)-2-(S)-Methylpropyl]-L-Prolinamide; (Benzyloxycarbonyl)-L-Valyl-N-[1-(3-(5-(benzyl)-1,2,4-oxadiazolyl)carbonyl)-2-(S)-Methylpropyl]-L-Prolinamide; (Benzyloxycarbonyl)-L-Valyl-N-[1-(3-(5-(3-methoxybenzyl)-1,2,4-oxadiazolyl)carbonyl)-2-(S)-Methylpropyl]-L-Prolinamide; (Benzyloxycarbonyl)-L-Valyl-N-[1-(3-(5-(2,6-difluorobenzyl)-1,2,4-oxadiazolyl) carbonyl)-2-(S)-Methylpropyl]-L-Prolinamide; (Benzyloxycarbonyl)-L-Valyl-N-[1-(3-(5-(trans-styryl)-1,2,4-oxadiazolyl)carbonyl)-2-(S)-Methylpropyl]-L-Prolinamide; (Benzyloxycarbonyl)-L-Valyl-N-[1-(3-(5-(trans-4-Trifluoro methylstyryl)-1,2,4-oxadiazolyl) carbonyl)-2-(S)-Methylpropyl]-L-Prolinamide; (Benzyloxycarbonyl)-L-Valyl-N-[1-(3-(5-(trans-4-Methoxystyryl)-1,2,4-oxadiazolyl)carbonyl)-2-(S)-Methylpropyl]-L-Prolinamide; (Benzyloxycarbonyl)-L-Valyl-N-[1-(3-(5-(3-Thienylmethyl)-1,2,4-oxadiazolyl) carbonyl)-2-(S)-Methylpropyl]-L-Prolinamide; (Benzyloxycarbonyl)-L-Valyl-N-[1-(3-(5-(Phenyl)-1,2,4-oxadiazolyl)carbonyl )-2-(S)-methylpropyl]-L-prolinamide; and (Benzyloxycarbonyl)-L-Valyl-N-[1-(3-(5-(3-Phenylpropyl)-1,2,4-oxadiazolyl)carbonyl)-2-(S)-Methylpropyl]-L-Prolinamide. U.S. Pat. No. 5,216,022 teaches other small molecules useful for the practice of this invention, including: Benzyloxycarbonyl-L-valyl-N-[1-(2-

[5-(3-methylbenzyl)-1,3,4-oxadiazolyl]carbonyl)-2-(S)-methylpropyl]-L-prolinamide (also known as CE-2072), Benzyloxycarbonyl-L-valyl-N-[1-(2-(3-methylbenzyl)-1,3,4-oxadiazolyl]carbonyl)-2-(S)-methylpropyl]-L-prolinamide; Benzyloxycarbonyl-L-valyl-N-[-(2-(5-(methyl)-1,3,4-oxadiazoly]carbonyl)-2-(S)-methylpropyl]-L-prolinamide; Benzyloxycarbonyl)-L-valyl-N-[1-(2-(5-(3-trifluoromethylbenzyl)-1,3,4-oxadiazolyl]carbonyl)-2-(S)-methylpropyl]-L-prolinamide; (Benzyloxycarbonyl)-L-valyl-N-[1-(2-(5-(4-Dimethylamino benzyl)-1,3,4-oxadiazolyl]carbonyl)-2-(S)-methylpropyl]-L-prolinamide; Benzyloxycarbonyl)-L-valyl-N-[1-(2-(5-(1-napthylenyl)-1,3,4-oxadiazolyl]carbonyl)-2-(S)-methylpropyl]-L-prolinamide; (Benzyloxycarbonyl)-L-valyl-[1-(3-(5-(3,4-methylenedioxybenzyl)-1,2,4-oxadiazolyl]carbonyl)-2-(S)-methylpropyl]-L-prolinamide; Benzyloxycarbonyl)-L-valyl-N-[1-(3-(5-(3,5-dimethylbenzyl)-1,2,4-oxadiazolyl]carbonyl)-2-(S)-methylpropyl]-L-prolinamide; (Benzyloxycarbonyl)-L-valyl-N-[1-(3-(5-(3,5-dimethoxybenzyl)-1,2,4-oxadiazolyl]carbonyl)-2-(S)-methylpropyl]-L-prolinamide; (Benzyloxycarbonyl)-L-valyl-N-[1-(3-(5-(3,5-ditrifluoromethylbenzyl)-1,2,4-oxadiazolyl]carbonyl)-2-(S)-methylpropyl]-L-prolinamide; (Benzyloxycarbonyl)-L-valyl-N-[1-(3-(5-(3-methylbenzyl)-1,2,4-oxadiazolyl]carbonyl)-2-(S)-methylpropyl]-L-prolinamide; (Benzyloxycarbonyl)-L-valyl-N-[1-(3-(5-(biphenylmethine)-1,2,4-oxadiazolyl]carbonyl)-2-(S)-methylpropyl]-L-prolinamide; (Benzyloxycarbonyl)-L-valyl-N-[1-(3-(5-(4-phenylbenzyl)-1,2,4-oxadiazolyl]carbonyl)-2-(S)-methylpropyl]-L-prolinamide; (Benzyloxycarbonyl)-L-valyl-N-[1-(3-(5-(3-phenylbenzyl)-1,2,4-oxadiazolyl]carbonyl)-2-(S)-methylpropyl]-L-prolinamide; (Benzyloxycarbonyl)-L-valyl-N-[1-(3-(5-(3-phenoxybenzyl)-1,2,4-oxadiazolyl]carbonyl)-2-(S)-methylpropyl]-L-prolinamide; (Benzyloxycarbonyl)-L-valyl-N-[1-(3-(5-(cyclohexylmethylene)-1,2,4-oxadiazolyl]carbonyl)-2-(S)-methylpropyl]-L-prolinamide; (Benzyloxycarbonyl)-L-valyl-N-[1-(3-(5-(3-trifluoromethyldimethylmethylene )-1,2,4-oxadiazolyl]carbonyl)-2-(S)-methylpropyl]-L-prolinamide; (Benzyloxycarbonyl)-L-valyl-N-[1-(3-(5-(1-napthylmethylene)-1,2,4-oxadiazolyl]carbonyl)-2-(S)-methylpropyl]-L-prolinamide; (Benzyloxycarbonyl)-L-valyl-N-[1-(3-(5-(3-pyridylmethyl)-1,2,4-oxadiazolyl]carbonyl)-2-(S)-methylpropyl]-L-prolinamide; (Benzyloxycarbonyl)-L-valyl-N-[1-(3-(5-(3,5-diphenylbenzyl)-1,2,4-oxadiazolyl]carbonyl)-2-(S)-methylpropyl]-L-prolinamide; (Benzyloxycarbonyl)-L-valyl-N-[1-(3-(5-(4-dimethylaminobenzyl)-1,2,4-oxadiazolyl]carbonyl)-2-(S)-methylpropyl]-L-prolinamide; 2-(5-[(Benzyloxycarbonyl)amino]-6-oxo-2-(4-fluorophenyl)-1,6-dihydro-1-pyrimidinyl]-N-[1-(3-(5-(3-trifluoromethylbenzyl)-1,2,4-oxadiazolyl]carbonyl)-(S)-2-methylpropyl]acetamide; 2-(5-Amino-6-oxo-2-(4-fluorophenyl)-1,6-dihydro-1-pyrimidinyl]-N-[1-(3-(5-(3-trifluoromethylbenzyl)-1,2,4-oxadiazolyl]carbonyl)-2-(S)-methylpropyl]acetamide; 2-(5-[(Benzyloxycarbonyl)amino]-6-oxo-2-(4-fluorophenyl)-1,6-dihydro-1-pyrimidinyl]-N-[1-(2-(5-(3-methylbenzyl)-1,3,4-oxadiazolyl]carbonyl)-(S)-2-methylpropyl]acetamide; 2-(5-Amino-6-oxo-2-(4-fluorophenyl)-1,6-dihydro-1-pyrimidinyl]-N-[1-(2-(5-(3-methylbenzyl)-1,3,4-oxadiazolyl]carbonyl)-2-methylpropyl]acetamide; (Pyrrole-2-carbonyl)-N-(benzyl)glycyl-N-[1-(2-(5-(3-methylbenzyl)-1,3,4-oxadiazolyl]carbonyl)-2-(S)-methylpropyl]amide; (Pyrrole-2-carbonyl)-N-(benzyl)glycyl-N-[1-(3-(5-(3-trifluoromethylbenzyl))-1,2,4-oxadiazolyl)-(S)-methylpropyl]amide; (2S,5S)-5-Amino-1,2,4,5,6,7-hexahydroazepino-[3,2,1]-indole-4-one-carbonyl-N-[1-(2-(5-(3-methylbenzyl)-1,3 ,4-oxadiazolyl]carbonyl)-(R,S)-2-methylpropyl]amide; BTD-[1-(2-(5-(3-methylbenzyl)-1,3,4-oxadiazolyl]carbonyl)-2-(S)-methylpropyl]amide; (R,S)-3-Amino-2-oxo-5-phenyl-1,4,-benzodiazepine-N-[1-(2-(5-(3-methylbenzyl)-1,3,4-oxadiazolyl]carbonyl)-2-(S)-methylpropyl]acetamide; (Benzyloxycarbonyl)-L-valyl-2-L-(2,3-dihydro-1H-indole)-N-[1-(2-(5-(3-methylbenzyl)-1,3,4-oxadiazolyl]carbonyl)-2-(S)-methylpropyl]amide; (Benzyloxycarbonyl)-L-valyl-2-L-(2,3-dihydro-1H-indole)-N-[1-(3-(5-(3-trifluoromethylbenzyl)-1,2,4-oxadiazolyl]carbonyl)-2-(S)-methylpropyl]amide; Acetyl-2-L-(2,3-dihydro-1H-indole)-N-[1-(2-(5-(3-methylbenzyl)-1,3,4-oxadiazolyl]carbonyl)-2-(S)-methylpropyl]amide; 3-(S)-(Benzyloxycarbonyl) amino)-ϵ-lactam-N-[1-(2-(5-(3-methylbenzyl)-1,3,4-oxadiazolyl]carbonyl)-2-(S)-methylpropyl]acetamide; 3-(S)-(Amino)-ϵ-lactam-N-[1-(2-(5-(3-methylbenzyl)-1,3,4-oxadiazolyl]carbonyl)-2-(S)-methylpropyl]acetamide trifluoroacetic acid salt; 3-(S)-[(4-morpholino carbonyl-butanoyl)amino]-ϵ-lactam-N-[1-(2-(5-(3-methylbenzyl)-1,3,4-oxadiazolyl]carbonyl)-2-(R,S)-methylpropyl] acetamide; 6-[4-Fluorophenyl)-ϵ-lactam-N-[1-(2-(5-(3-methylbenzyl)-1,3,4-oxadiazolyl]carbonyl)-2-(S)-methylpropyl]acetamide; 2-(2-(R,S)-Phenyl-4-oxothiazolidin-3-yl]-N-[1-(2-(5-(3-methylbenzyl)-1,3,4-oxadiazolyl]carbonyl)-2-(S)-methylpropyl]acetamide; 2-(2-(R,S)-phenyl-4-oxothiazolidin-3-yl]-N-[1-(2-(5-(3-methylbenzyl)-1,3,4-oxadiazolyl]hydroxymethyl)-2-(S)-methylpropyl]acetamide; 2-(2-(R,S)-Benzyl-4-oxothiazolidin-3-yl]-N-[1-(2-(5-(3-methylbenzyl)-1,3,4-oxadiazolyl]carbonyl)-2-(S)-methylpropyl]-acetamide; 2-(2-(R,S)-Benzyl-4-oxothiazolidin-3-yl oxide]-N-[1-(3-(5-(3trifluoromethylbenzyl)-1,2,4-oxadiazolyl]carbonyl)-2-(R,S,)-methylpropyl]acetamide; (1-Benzoyl-3,8-quinazolinedione)-N-[1-(2-(5-(3-methylbenzyl)-1,3,4-oxadiazolyl]carbonyl)-2-(S)-methylpropyl]acetamide; (1-Benzoyl-3,6-piperazinedione)-N-[1-(2-(5-(3-methylbenzyl)-1,3,4-oxadiazolyl]carbonyl)-2-(S)-methylpropyl]acetamide; (1-Phenyl-3,6-piperazinedione)-N-[1-(2-(5-(3-methylbenzyl)-1,3,4-oxadiazolyl]carbonyl)-2-(S)-methylpropyl]acetamide; [(1-Phenyl-3,6-piperazinedione)-N-[1-(3-(5-(3-trifluoromethylbenzyl))-1,2,4-oxadiazolyl]carbonyl)]-2-(S)-methylpropyl]acetamide; 3-[(Benzyloxycarbonyl)amino]-quinolin-2-one-N-[1-(2-(5-(3-methylbenzyl)-1,3,4-oxadiazolyl]carbonyl)-2-(S)-methylpropyl]acetamide; 3-[(Benzyloxycarbonyl)amino]-7-piperidinyl-quinolin-2-one-N-[1-(2-(5-(3-methylbenzyl)-1,3,4-oxadiazolyl]carbonyl)-2-(S)-methylpropyl]acetamide; 3-(Carbomethoxy-quinolin-2-one-N-[1-(2-(5-(3-methybenzyl)-1,3,4-oxadiazoly l]carbonyl)-2-(S)-methylpropyl]acetamide; 3-(Amino-quinolin-2-one)-N-[1-(2-(5-(3-methylbenzyl)-1,3,4-oxadiazolyl]carbonyl)-2-(S)-methylpropyl]acetamide; 3-[(4-Morpholino)aceto]amino-quinolin-2-one-N-[1-(2-(5-(3-methylbenzyl)-1,3,4-oxadiazolyl]carbonyl)-2-(S)-methylpropyl]acetamide; 3,4-Dihydro-quinolin-2-one-N-[1-(2-(5-(3-methylbenzyl)-1,3,4-oxadiazolyl]carbonyl)-2-(S)-methylpropyl]acetamide; 1-Acetyl-3-(4-fluorobenzylidene) piperazine-2,5-dione-N-[1-(2-(5-(3-methylbenzyl)-1,3,4-oxadiazolyl]carbonyl)-2-(S)-methylpropyl]acetamide; 1-Acetyl-3-(4-dimethylamino benzylidene)piperazine-2,5-dione-N-[1-(2-(5-(3-methylbenzyl)-1,3,4-oxadiazolyl]carbonyl)-2-(S)-methylpropyl]acetamide; 1-Acetyl-3-(4-carbomethoxy benzylidene)piperazine-2,5-dione-N-[1-(2-(5-(3-methylbenzyl)-1,3,4-oxadiazolyl]carbonyl)-2-(S)- methylpropyl]acetamide; 1-Acetyl-3-[(4-pyridyl) methylene]piperazine-2,5-dione-N-[1-(2-(5-(3-methyl benzyl)-1,3,4-oxadiazolyl]carbonyl)-2-(S)-methylpropyl] acetamide; 4-[1-Benzyl-3-(R)-benzyl-piperazine-2,5,-dione]-N-[1-(2-[5-(3-methylbenzyl)-1,3,4-oxadiazolyl] carbonyl)-2-methylpropyl]acetamide; 4-[1-Benzyl-3-(S)-benzyl piperazine-2,5,-dione]-N-[1-(2-(5-(3-methylbenzyl)-1,3,4-oxadiazolyl]carbonyl)-2-(S)-methylpropyl]acetamide; 4-[1-Benzyl-3(R)-benzylpiperazine-2,5,-dione]-N-[1-(3-(5-(3-trifluoromethylbenzyl)-1,2,4-oxadiazolyl]carbonyl)-2-(S)-methylpropyl]acetamide; 4-[1-Benzyl-3-(S)-benzylpiperazine-2,5,-dione]-N-[1-(3-(5-(3-trifluoromethylbenzyl)-1,2,4-oxadiazolyl]carbonyl)-2-(S)-methylpropyl]acetamide; 4-[1-Benzyl-3-(S)-benzyl piperazine-2,5,-dione]-N-[1-(3-(5-(2-dimethylaminoethyl)-1,2,4-oxadiazolyl ]carbonyl)-2-(S)-methylpropyl] acetamide; 4-[1-Methyl-3-(R,S)-phenylpiperazine-2,5,-dione]-N-[1-(3-(5-(3-trifluoromethylbenzyl)-1,2,4-oxadiazolyl]carbonyl)-2-(S)-methylpropyl]acetamide; 4-[[-Methyl-3-(R,S)-phenyl piperazine-2,5,-dione]-N-[1-(2-(5-(3-methylbenzyl)-1,3,4-oxadiazolyl]carbonyl)-2-(S)-methylpropyl]acetamide; 4-[1-(4-Morpholino ethyl)3-(R)-benzyl piperazine-2,5,-dione]-N-[1-(2-(5-(3-methylbenzyl)-1,3,4-oxadiazolyl]carbonyl)-2-(S)-methylpropyl]acetamide; 5-(R,S)-Phenyl-2,4-imidazolidinedione-N-[1-(2-(5-(3-methylbenzyl)-1,3,4-oxadiazolyl]carbonyl)-2-(S)-methylpropyl]acetamide; 5-(R)-Benzyl-2,4-imidazolidinedione-N-[1-(2-(5-(3-methylbenzyl)-1,3,4-oxadiazolyl]carbonyl)-2-(S)-methylpropyl]acetamide; 5-(S)-Benzyl-2,4-imidazolidinedione-N-[1-(2-(5-(3-methylbenzyl)-1,3,4-oxadiazolyl]carbonyl)-2-(S)-methylpropyl]acetamide; 5-(S)-Benzyl-2,4-imidazolidinedione-N-[1-(3-(5-(3-trifluoromethylbenzyl)-1,2,4-oxadiazolyl]carbonyl)-2-(S)-methylpropyl]acetamide; 5-(R)-Benzyl-2,4-imidazolidinedione-N-[1-(3-(5-(3-trifluoromethylbenzyl)-1,2,4-oxadiazolyl]carbonyl)-2-(S)-methylpropyl]acetamide; 1-Benzyl-4-(R)-benzyl-2,5-imidazolidinedione-N-[1-(2-(5-(3-methylbenzyl)-1,3,4-oxadiazolyl]carbonyl)-2-(S)-methylpropyl]acetamide; and 1-Benzyl-4-(R)-benzyl-2,5-imidazolidinedione-N-[1-(3-(5-(3-trifluoromethyl benzyl)-1,2,4-oxadiazolyl]carbonyl)-2-(S)-methylpropyl]acetamide among others.

Likewise, U.S. Pat. No. 5,869,455 discloses N-substituted derivatives; U.S. Pat. No. 5,861,380 protease inhibitors-keto and di-keto containing ring systems; U.S. Pat. No. 5,807,829 serine protease inhibitor-tripeptoid analogues; U.S. Pat. No. 5,801,148 serine protease inhibitors-proline analogues; U.S. Pat. No. 5,618,792 substituted heterocyclic compounds useful as inhibitors of serine proteases. These patents and PCT publications and others as listed infra are incorporated herein, in their entirety, by reference. Other equally advantageous molecules, which may be used instead of $\alpha_1$-antitrypsin or in combination with $\alpha_1$-antitrypsin are contemplated such as in WO 98/20034 disclosing serine protease inhibitors from fleas. Without limiting to this single reference one skilled in the art can easily and without undue experimentation adopt compounds such as in WO98/23565 which discloses aminoguanidine and alkoxyguanidine compounds useful for inhibiting serine proteases; WO98/50342 discloses bis-aminomethylcarbonyl compounds useful for treating cysteine and serine protease disorders; WO98/50420 cyclic and other amino acid derivatives useful for thrombin-related diseases; WO 97/21690 D-amino acid containing derivatives; WO 97/10231 ketomethylene group-containing inhibitors of serine and cysteine proteases; WO 97/03679 phosphorous containing inhibitors of serine and cysteine proteases; WO 98/21186 benzothiazo and related heterocyclic inhibitors of serine proteases; WO 98/22619 discloses a combination of inhibitors binding to P site of serine proteases with chelating site of divalent cations; WO 98/22098 a composition which inhibits conversion of pro-enzyme CPP32 subfamily including caspase 3 (CPP32/Yama/Apopain); WO 97/48706 pyrrolo-pyrazine-diones; WO 97/33996 human placental bikunin (recombinant) as serine protease inhibitor; WO 98/46597 complex amino acid containing molecule for treating viral infections and conditions disclosed hereinabove.

Other compounds having serine protease inhibitory activity are equally suitable and effective, including but not limited to: tetrazole derivatives as disclosed in WO 97/24339; guanidinobenzoic acid derivatives as disclosed in WO 97/37969 and in a number of U.S. Pat. Nos. 4,283,418; 4,843,094; 4,310,533; 4,283,418; 4,224,342; 4,021,472; 5,376,655; 5,247,084; and 5,077,428; phenylsulfonylamide derivatives represented by general formula in WO 97/45402; novel sulfide, sulfoxide and sulfone derivatives represented by general formula in WO 97/49679; novel amidino derivatives represented by general formula in WO 99/41231; other amidinophenol derivatives as disclosed in U.S. Pat. Nos. 5,432,178; 5,622,984; 5,614,555; 5,514,713; 5,110,602; 5,004,612; and 4,889,723 among many others.

5.3. Serine Protease Inhibitors with Free Radical Scavengers and Antioxidants

As agents that affect NO levels may not directly prevent the oxidizing and free radical action of NO and its metabolites, it is preferable to administer two or three independently acting agents than a single agent. Therefore one preferred embodiment of the process is the administration of both a serine protease inhibitor and an antioxidant, a nitric oxide scavenger, or a peroxynitrite scavenger.

Preferred peroxynitrite scavengers are 2,6,8-trihydroxypurine (uric acid), dihydrorhodamine, and compounds that contain a thiol group (especially glutathione or cysteine). Uric acid is also considered to be an hydroxyl radical scavenger.

Anti-oxidants, including, but not limited to vitamin A, vitamin E, vitamin C, cysteine, ω-3-unsaturated lipids, ω-6-unsaturated lipids, alpha-carotenes, beta-carotenes, selenium, curcumin, a superoxide dismutase preparation, ginkgo biloba, lycopenes, glutathione, bioflavenoids, catechins, lignans, linolenic acid, quercetin, zeaxanthin, or combinations or complexes thereof, may be used with the protease inhibitors of the invention.

In yet another embodiment of the invention, superoxide-resistant AAT enzymes and forms of AAT are used to avoid inactivation by excess NO. As an example, synthetic AAT or recombinant AAT produced with alternative and oxidation-resistant amino acid sequences are embodiments of the invention.

5.4 Inhibitors of NO and the Sparing of AAT

NO may result in synthesis of ONOO⁻, which is know to inactivate $\alpha_1$-antitrypsin. Therefore, any agent that replenishes $\alpha_1$-antitrypsin activity through inhibition of NO production will ameliorate diseases resulting from reduced $\alpha_1$-antitrypsin activity. One embodiment of the invention is the use of inhibitors of NO synthesis to indirectly protect levels of active $\alpha_1$-antitrypsin. Many inhibitors of NO are useful in this embodiment including derivatives of amino acids, for example $N^G$-nitro-L-arginine methyl ester (L-NAME), $N^G$-nitro-L-arginine (L-NA), $N^G$-methyl-L-arginine (L-NMA), N,N'-dimethylarginine, $N^G$-monoethyl-L-arginine acetate, $N^G$-monomethyl-L-arginine acetate, $N^G$-monomethyl-D-arginine, $N^G$-monomethyl-L-homoarginine acetate, $N^G$-nitro-D-arginine, $N^G$-nitro-D- arginine methyl ester hydrochloride, -nitro-L-arginine, and L-N⁶-(1-iminoethyl)lysine, and salts thereof. Likewise, non-amino acid inhibitors of NO are equally useful in the instant invention, including, but not limited to, guanidine and guanidine derivatives, S-alkylisothioureas, amidines, imidazoles, indazoles, and mercapto-alkylguanidines, and salts thereof. Examples of non-amino acid NO inhibitors include aminoguanidine, S-methylisothiourea sulfate, S-ethylisothiourea sulfate, S-aminoethylisothiourea sulfate, mercaptoethylguanidine, 2,4-diamino-6-hydroxypyrimidine, diphenyleneiodonium chloride, 2-ethyl-2-thiopseudourea hydrobromide,2-iminobiotin, L-N⁵-(1-iminoethyl)ornithine hydrochloride, S-methyl-L-thiocitrulline dihydrochloride, p-nitroblue tetrazolium chloride, 3-bromo-7-nitroindazole, pentamidine isethionate, 1-pyrrolidinecarbodithioic acid, spermidine, spermine, spermine-NO, 3-morpholinosydonimine-N-ethyl-carbamide, L-thiocitrulline, troleandomycin, and 7-nitroindazole, and salts thereof, but the invention is not limited to these named examples. Furthermore agents that bind NO are suitable for this embodiment of the invention and these agents can include, for example, heme-containing proteins including hemoglobin, myoglobin, cytochrome V, guanylyl cyclase, NADH:ubiquinone oxidoreductase, NADH:succinate oxidoreductase and cis-aconitase, and salts thereof. Certain agents that ordinarily function as donors of NO also have a paradoxical effect on the inhibition of NOS and are suitable for use in the sparing of α₁-antitrypsin. Suitable NO donor agents include S-nitroso-N-acetylpenicillamine, S-nitrosoglutathione and nitroglycerine.

5.5. Diseases Addressed by the Invention

Specific diseases or disorders for which the therapeutic methods of the invention are beneficial include but are not limited to inflammatory diseases or disorders, hypotension, and the like. The disease or disorder can be selected from the group consisting of but not limited to acquired tubulointerstitial disease, acute pancreatitis, acute respiratory failure, acute respiratory distress syndrome (ARDS), age-associated memory impairment, AIDS, airway inflammation, Alzheimer's disease, amyotrophic lateral sclerosis, asthma, atherosclerosis, autoimmune disease, myocarditis, carcinogenesis, cerebral ischemia, cerebrovascular disease, chronic liver disease, chronic lung disease, chronic obstructive pulmonary disease, chronic otitis media, congestive heart failure, coronary artery disease, coronary artery ectasia, diabetes mellitus, diabetic neuropathy, dysfunctional uterine bleeding, dysmenorrhea, endotoxic shock, end-stage renal disease, falciparum malaria, gastric carcinogenesis, gastrointestinal pathophysiology, glaucoma, glutamate-induced asthma, glutamate induced Chinese restaurant syndrome, heart failure, heat stress, gastritis, 'hot-dog headache', Hirschsprung's disease, HIV infection, hypertension, hypoxemic respiratory failure, inflammatory arthritis, inflammatory bowel disease (Crohn's disease and ulcerative colitis), inflammatory joint diseases, liver cirrhosis, liver disease, Lyme neuroborreliosis, migraine, multiple sclerosis, neonatal and pediatric respiratory failure, nephrotoxicity, neurodegenerative diseases, orthopedic disease, osteoarthritis, oxidant stress, Parkinson's disease, pediatric pulmonary disease, pleural inflammation, preeclampsia, primary ciliary dyskinesia, primary pulmonary hypertension, protozoan infections, pugilistic Alzheimer's disease, pulmonary hypertension, retinal disease, septic shock, sickle cell anemia, rheumatoid arthritis, stroke, systemic lupus erythematosus, traumatic brain injury, tumor progression, or vascular disease. These diseases are thought to be mediated, at least in part, by aberrant levels of nitric oxide. In specific embodiments, the inflammatory disease or disorder is mediated at least in part by an agent selected from the group consisting of γ-interferon and lipopolysaccharide.

As noted above, the present invention can be used in the treatment of hypotension, including but not limited to hypotension resulting from septic, endotoxic, hypovolemic, or traumatic shock, chronic hypotension, and disorders associated with hypotension, such as priapism. Accordingly, the invention further provides for administering an amount of a vasoconstrictor NO antagonist effective to increase blood pressure in an animal in addition to or in conjunction with administration of a serine protease inhibitor. Suitable vasoconstrictors include, but are not limited to, epinephrine; norepinephrine; vasopressin; $N^G$-monomethyl-L-arginine (L-NMA); $N^G$-nitroarginine methyl ester (L-NAME), and thromboxane-$A_2$.

Additionally, a representative sample of diseases that the methods and compositions of the invention are to treat are listed in Table 1.

TABLE 1

Diseases Related to Excess NO

| NO Effect | Disease(s) |
| --- | --- |
| Decreased Blood pressure (vasodilation) | Sepsis, septic shock, ARDS (shock lung), acute renal failure, shock liver, acute ischemic bowel injury |
| Decreased cardiac output | Myocardial depression of sepsis, acute and chronic congestive heart failure |
| HIV production | HIV infection, AIDS |
| Production of ONOO- (peroxynitrite) and reactive oxygen intermediates | 1. Ischemic brain injury 2. HIV-induced encephalopathy and dementia 3. Ischemia-reperfusion injury (myocardial infarction, cerebrovascular accident/stroke) |
| Production of ONOO- (peroxynitrite) and reactive oxygen intermediates, resulting in reduced AAT activity | 1. HIV infection/AIDS 2. CMV infection 3. Herpes simplex 1 and 2 infections 4. Influenza infection 5. Apoptosis-associated diseases |
| Direct toxicity | Neurotoxicity |
| Epithelial Damage | 1. Cystic fibrosis 2. Interstitial pulmonary fibrosis |
| Inflammation | 1. Asthma 2. Pulmonary embolism |

5.6. Therapeutic Methods

According to the present invention, NO production is inhibited to obtain important therapeutic benefits. Nitric oxide activity can be associated with inflammation, septic shock, adverse consequences of ischemia and reperfusion injury, hypotension, and cell death, to mention a few indications.

Inflammation involves cell-mediated immune response, with release of toxic molecules including NO. Of particular importance in the inflammatory response are macrophagic cells and endothelium, and the invention is particularly directed to inhibiting NO production by these cells. Cell mediated immune response can be beneficial, e.g., for destroying infectious microorganisms such as bacteria and parasites, and for eliminating cancerous or virally infected cells. However, inflammation can become chronic, autoimmune, and detrimental. Therefore, the methods and compositions of the invention can be useful for treating inflammation, for example, lung inflammation, including but not limited to asthma; liver inflammation; acne, inflammatory bowel disease; arthritis; and the like. NO inhibitory activity of the molecules of the invention can be administered either as a primary therapy or in conjunction with other anti-inflammatory therapies, including, but not limited to, steroid treatment, immune-cell targeted antibody therapy, and the like.

Septic shock results from the host response to systemic bacterial infection, particularly to bacterial endotoxins, such as Gram negative lipopolysaccharides. Nitric oxide overproduction contributes to septic shock. Any reduction in NO production will have an ameliorating effect on the symptoms of septic shock. The invention thus provides for administration of $\alpha_1$-antitrypsin, or a fragment, derivative or analog thereof, for the treatment of septic shock, whether as a primary therapy or in conjunction with other therapies, e.g., antibodies to lipopolysaccharide, antibodies to tumor necrosis factor or interleukin-1, interleukin-1 receptor antagonist, or soluble TNF or IL-1 receptors. Macrophages and endothelium are particular cellular targets for inhibition of NO activity. To date, septic shock in humans has proved to be highly refractory to therapy. Therefore, it is a particular advantage of the invention to provide a therapy or co-therapy for septic shock.

NO has been associated with the adverse effects of ischemic events. Ischemia, or reduced blood perfusion of tissues, results in hypoxia and is a particularly serious problem when it occurs in the heart, e.g., as a consequence of myocardial infarct or after balloon angioplasty; in the brain, e.g., as a consequence of stroke; in the lungs; and in the kidneys. Therefore, administration of a dosage of the invention would greatly benefit a subject suspected of suffering from ischemia or reperfusion injury. Preferably, the dosage of serine protease inhibitor/NO inhibitory agent is administered prior to or concomitant with any drugs designed to release the blockage causing the ischemic condition. In a specific embodiment, $\alpha_1$-antitrypsin, or a fragment, derivative or analog thereof is administered prior to, or with, tissue plasminogen activator (tPA), streptokinase, and the like for treating myocardial infarct. The combination of a serine protease inhibitor and/or NO inhibitory agent with tPA, streptokinase, and the like, can reduce inflammation and NO production and apoptosis associated with the infarct because NO and free radical production occur during ischemia/reperfusion. The serine protease inhibitor, NOS inhibitor and/or other agents are advantageously administered within about the first four hours of ischemia, preferably within the first hour after ischemia, and most preferably concurrent with the ischemic event. These same inhibitors can also be administered prior to an anticipated ischemic event. Ischemic events can be anticipated in some patients in groups at risk. Patients undergoing angioplasty are in such a category, and patients undergoing many other types of surgery have an elevated risk. Also, patients who are at risk because of clotting disorders, arteriosclerosis, or a history of transient ischemic attacks (TIAs) would be candidates for preventative treatment. Patients in a high risk category for ischemia can be treated chronically. Endogenous AAT can be inactivated, e.g. by NO and free radicals, during reperfusion. This loss of AAT activity will exacerbate NO production, inflammation, and apoptosis. Therefore, administration of exogenous AAT, an oxidation-resistant mutant AAT, or an oxidation-resistant synthetic analog will be especially beneficial.

Hypotension, or low blood pressure, can cause problems with circulation. Hypotension and shock can result from sepsis, severe blood loss, serious organ injury, severe trauma and chemotherapy, particularly cytokine-based chemotherapy. Thus, the present invention provides for treatment of severe hypotension. In a specific embodiment, priapism (impotence) associated with hypotension can be treated. In another specific embodiment, hypotensive shock that may result from administration of IL-2 or TNF to treat cancer can be ameliorated. In ischemic injury, NO induces neurotoxicity. An embodiment of this invention reduces neurotoxicity by administration of inhibitors of NOSs and/or by administration of NO inhibitors.

NO is an active neurotransmitter. Excessive production or activity of NO may result in neurological diseases, particularly those affecting the brain. Therefore, administration of a dosage of the invention composition, i.e., $\alpha_1$-antitrypsin, or a fragment, derivative or analog thereof, can be beneficial for the treatment of neurological diseases or disorders. In a preferred aspect, the agent is an analog of $\alpha_1$-antitrypsin that can cross the blood brain barrier, which would allow for intravenous or oral administration. Many strategies are available for crossing the blood brain barrier, including but not limited to, increasing the hydrophobic nature of a molecule; introducing the molecule as a conjugate to a carrier, such as transferrin, targeted to a receptor in the blood brain barrier; and the like. In another embodiment, the agent can be administered intracranially or, more directly, intraventricularly.

In a further embodiment, the methods and compositions of the invention are useful in the therapeutic treatment of diseases or disorders of the kidney. Glomerulonephritis is characterized by enhanced production of NO, which may contribute to tissue injury. During inflammation, reperfusion, or other stress related processes, kidney cells are exposed to an array of factors and mediators that can stimulate excessive NO production. Excessive NO production results in increases in reactive intermediates, which can damage kidney tissues. Enhanced NO production is also a serious consequence of uremia. Thus, the present invention provides for the amelioration or alleviation of many diseases of the kidney.

Ischemia-induced lung injury (shock lung), also known as acute respiratory distress syndrome, is a candidate for therapeutic intervention using serine protease inhibitors, especially serine protease inhibitors that are resistant to inactivation by reactive oxygen intermediates.

Certain metastatic diseases can also be treated by administration of $\alpha_1$-antitrypsin, according to the present invention. For example, inhibition of NO activity, which can result in reduced blood flow, may aid in a treatment of solid tumors that involves or is enhanced by hypoxia.

The therapeutic methods and compositions of the invention may also be useful for the treatment of altitude sickness. Altitude sickness is thought to result from reduced oxygen tension and consequential hypoxia of certain tissues, particularly the lungs and brain. According to the present invention, administration of $\alpha_1$-antitrypsin, or a fragment, derivative or analog thereof, may alleviate the symptoms of altitude sickness.

In a further embodiment, diseases or disorders associated with NO can be treated by administering a substance that induces $\alpha_1$-antitrypsin expression rather than by directly administering $\alpha_1$-antitrypsin.

In a yet further embodiment, diseases can be prevented by the timely administration of the agent of the invention as a prophylactic, prior to onset of symptoms, or signs, or prior to onset of severe symptoms or signs. Thus, a patient at risk for a particular disease caused in part by excessive NO levels or excessive NOS expression, can be treated with serine protease inhibitors, for example, (Benzyloxycarbonyl)-L-Valyl-N-[1-(3-(5-(3-Trifluoromethylbenzyl)-1,2,4- oxadiazolyl)carbonyl)-2-(S)-Methylpropyl]-L-Prolinamide; as a precautionary measure.

The effective dose of the agent of the invention, and the appropriate treatment regime, can vary with the indication and patient condition, and the nature of the molecule itself, e.g., its in vivo half life and level of activity. These parameters are readily addressed by one of ordinary skill in the art and can be determined by routine experimentation.

The preferred doses for administration can be anywhere in a range between about 0.01 mg and about 20 mg per ml of biologic fluid of treated patient. The therapeutically effective amount of $\alpha_1$-antitrypsin, peptides, or drugs that have similar activities as $\alpha_1$-antitrypsin or peptides can be also measured in molar concentrations and can range between about 1 nM to about 2 mM.

The therapeutic agents of the instant invention may be used for the treatment of animal subjects or patients, and more preferably, mammals, including humans, as well as mammals such as non-human primates, dogs, cats, horses, cows, pigs, guinea pigs, and rodents.

In another embodiment of the invention a mechanical device is used to reestablish blood flow, in conjunction with administration of any inhibitor of serine protease, including, but not limited to $\alpha_1$-antitrypsin and Benzyloxycarbonyl-L-valyl-N-[1-(2-(3-methylbenzyl)-1,3,4-oxadiazolyl] carbonyl)-2-(S)-methylpropyl]-L-prolinamide. The mechanical device can be, for example, a stent, or involve, for example, percutaneous transluminal coronary angioplasty (PTCA) or angioplasty.

5.7. Modes of Administration

Modes of administration of the various therapeutic agents used in the invention are exemplified below. However, the agents can be delivered by any of a variety of routes including: by injection (e.g., subcutaneous, intramuscular, intravenous, intraarterial, intraperitoneal), by continuous intravenous infusion, transdermally, orally (e.g., tablet, pill, liquid medicine), by implanted osmotic pumps (e.g., Alza Corp.), by suppository or aerosol spray.

The peptide-based serine protease inhibitors may be prepared by any suitable synthesis method such as originally described by Merrifield, *J. Am. Chem. Soc.*, 85, p 2149 (1963). Synthetic peptides which exhibit inhibitory activity toward serine proteases and methods for preparing and using same are disclosed for example in U.S. Pat. Nos. 4,829,052, 5,157,019 to Glover; U.S. Pat. No. 5,420,110 to Miller; U.S. Pat. No. 4,963,654 Katunuma as incorporated herein by reference Those skilled in the art of biochemical synthesis will recognize that for commercial-scale quantities of peptides, such peptides are preferably prepared using recombinant DNA techniques, synthetic techniques, or chemical derivatization of biologically or chemically synthesized peptides.

The compounds of the present invention are used as therapeutic agents in the treatment of a physiological (especially pathological) condition caused in whole or part, by uncontrolled serine protease and NO activity. The peptides may be administered as free peptides or pharmaceutically acceptable salts thereof. The terms used herein conform to those found in Budavari, Susan (Editor), "The Merck Index" An Encyclopedia of Chemicals, Drugs, and Biologicals; Merck & Co., Inc. The term "pharmaceutically acceptable salt" refers to those acid addition salts or metal complexes of the peptides which do not significantly or adversely affect the therapeutic properties (e.g. efficacy, toxicity, etc.) of the peptides. The peptides should be administered to individuals as a pharmaceutical composition, which, in most cases, will comprise the peptide and/or pharmaceutical salts thereof with a pharmaceutically acceptable carrier. The term "pharmaceutically acceptable carrier" refers to those solid and liquid carriers, which do not significantly or adversely affect the therapeutic properties of the peptides.

The pharmaceutical compositions containing peptides of the present invention may be administered to individuals, particularly humans, either intravenously, subcutaneously, intramuscularly, intranasally, orally, topically, transdermally, parenterally, gastrointestinally, transbronchially and transalveolarly. Topical administration is accomplished via a topically applied cream, gel, rinse, etc. containing therapeutically effective amounts of inhibitors of serine proteases. Transdermal administration is accomplished by application of a cream, rinse, gel, etc. capable of allowing the inhibitors of serine proteases to penetrate the skin and enter the blood stream. Parenteral routes of administration include, but are not limited to, direct injection such as intravenous, intramuscular, intraperitoneal or subcutaneous injection. Gastrointestinal routes of administration include, but are not limited to, ingestion and rectal. Transbronchial and transalveolar routes of administration include, but are not limited to, inhalation, either via the mouth or intranasally and direct injection into an airway, such as through a tracheotomy, tracheostomy, or endotracheal tube. In addition, osmotic pumps may be used for administration. The necessary dosage will vary with the particular condition being treated, method of administration and rate of clearance of the molecule from the body.

Although the compounds described herein and/or their derivatives may be administered as the pure chemicals, it is preferable to present the active ingredient as a pharmaceutical composition. The invention thus further provides the use of a pharmaceutical composition comprising one or more compounds and/or a pharmaceutically acceptable salt thereof, together with one or more pharmaceutically acceptable carriers therefor and, optionally, other therapeutic and/or prophylactic ingredients. The carrier(s) must be acceptable in the sense of being compatible with the other ingredients of the composition and not deleterious to the recipient thereof.

Pharmaceutical compositions include those suitable for oral or parenteral (including intramuscular, subcutaneous and intravenous) administration. The compositions may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combinations thereof, and then, if necessary, shaping the product into the desired delivery system.

Pharmaceutical compositions suitable for oral administration may be presented as discrete unit dosage forms such as hard or soft gelatin capsules, cachets or tablets, each containing a predetermined amount of the active ingredient; as a powder or as granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art., e.g., with enteric coatings.

Oral liquid preparations may be in the form of, for example, aqueous or oily suspension, solutions, emulsions, syrups or elixirs, or may be presented as a dry product for constitution with water or another suitable vehicle before use. Such liquid preparations may contain conventional additives such as suspending agents, emulsifying agents, non-aqueous vehicles (which may include edible oils), or preservative.

The compounds may also be formulated for parenteral administration (e.g., by injection, for example, bolus injection or continuous infusion) and may be presented in unit dose form in ampoules, pre-filled syringes, small bolus infusion containers or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the compounds may be formulated as ointments, creams or lotions, or as the active ingredient of a transdermal patch. Suitable transdermal delivery systems are disclosed, for example, in Fisher et al. (U.S. Pat. No. 4,788,603) or Bawas et al. (U.S. Pat. Nos. 4,931,279, 4,668,504 and 4,713,224). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredient can also be delivered via iontophoresis, e.g., as disclosed in U.S. Pat. Nos. 4,140,122, 4,383,529, or 4,051,842. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

Compositions suitable for topical administration in the mouth include unit dosage forms such as lozenges comprising active ingredient in a flavored base, usually sucrose and acacia or tragacanth; pastilles comprising the active ingredient in an inert base such as gelatin and glycerin or sucrose and acacia; mucoadherent gels, and mouthwashes comprising the active ingredient in a suitable liquid carrier.

When desired, the above-described compositions can be adapted to provide sustained release of the active ingredient employed, e.g., by combination thereof with certain hydrophilic polymer matrices, e.g., comprising natural gels, synthetic polymer gels or mixtures thereof.

The pharmaceutical compositions according to the invention may also contain other adjuvants such as flavorings, coloring, antimicrobial agents, or preservatives.

It will be further appreciated that the amount of the compound, or an active salt or derivative thereof, required for use in treatment will vary not only with the particular salt selected but also with the route of administration, the nature of the condition being treated and the age and condition of the patient and will be selected, ultimately, at the discretion of the attendant physician.

A pharmaceutical composition of the invention contains an appropriate pharmaceutically acceptable carrier as defined supra. These compositions can take the form of solutions, suspensions, tablets, pills, capsules, powders, sustained-release formulations and the like. Suitable pharmaceutical carriers are described in Remington's Pharmaceutical Sciences 1990, pp. 1519–1675, Gennaro, A. R., ed., Mack Publishing Company, Easton, Pa. The serine protease inhibitor molecules of the invention can be administered in liposomes or polymers (see, Langer, R. Nature 1998, 392, 5). Such compositions will contain an effective therapeutic amount of the active compound together with a suitable amount of carrier so as to provide the form for proper administration to the subject.

In general, the compound is conveniently administered in unit dosage form; for example, containing 5 to 2000 mg, conveniently 10 to 1000 mg, most conveniently, 50 to 500 mg of active ingredient per unit dosage form.

Desirable blood levels may be maintained by continuous infusion to provide about 0.01–5.0 mg/kg/hr or by intermittent infusions containing about 0.4–20 mg/kg of the active ingredient(s). Buffers, preservatives, antioxidants and the like can be incorporated as required.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations, such as multiple inhalations from an insufflator or by application of a plurality of drops into the eye.

6. EXAMPLES

The following specific examples are provided to better assist the reader in the various aspects of practicing the present invention. As these specific examples are merely illustrative, nothing in the following descriptions should be construed as limiting the invention in any way. Such limitations are, or course, defined solely by the accompanying claims.

6.1. Effect of $\alpha_1$-Antitrypsin on Nitric Oxide (NO) Production

RAW 264.5 macrophages are selected for measuring the effect of $\alpha_1$-antitrypsin on NO release. RAW 264.7 cell monolayers are pretreated for 1 hour with $\alpha_1$-antitrypsin (0.1–3 mg/ml), followed by costimulation by interferon-$\gamma$ (10 U/ml), and LPS (1 ng/ml) for 18 hours. Aliquots (100 $\mu$l) of supernatant are combined with equal volumes of Greiss reagent and incubated at room temperature for 10 minutes. The colorimetric determination of nitrite concentration is measured by absorbance at 550 nm and quantified with a standard curve. The combination of LPS and interferon-$\gamma$ is a potent stimulus for NO release in RAW 264.5 macrophages. The effect of $\alpha_1$-antitrypsin at 3 mg/ml on NO expression is measured.

6.2. Combined Effect of $\alpha_1$-Antitrypsin and an Antioxidant on Nitric Oxide (NO) Production RAW 264.7 cell monolayers are pretreated for 1 hour with seven concentrations of $\alpha_1$-antitrypsin (0.003, 0.01, 0.03, 0.1, 0.3, 1, and 3 mg/ml) in the absence or the presence of $\beta$-carotene (1 mg/ml), followed by costimulation by interferon-$\gamma$ (10 U/ml), and LPS (1 ng/ml) for 18 hours. Aliquots (100 $\mu$l) of supernatant are combined with equal volumes of Greiss reagent and incubated at room temperature for 10 minutes. The colorimetric determination of nitrite concentration is measured by absorbance at 550 nm and quantified with a standard curve. The effect of $\alpha_1$-antitrypsin in combination with $\beta$-carotene on NO release is compared to the effect of each agent individually.

6.3. Combined Effect of $\alpha_1$-Antitrypsin and a Free Radical Scavenger on Nitric Oxide (NO) Production RAW 264.7 cell monolayers are pretreated for 1 hour with seven concentrations of $\alpha_1$-antitrypsin (0.003, 0.01, 0.03, 0.1, 0.3, 1, and 3 mg/ml) in the absence or the presence of 2,6,8-trihydroxypurine (0.1 mg/ml), followed by costimulation by interferon-γ (10 U/ml), and LPS (1 ng/ml) for 18 hours. Aliquots (100 μl) of supernatant are combined with equal volumes of Greiss reagent and incubated at room temperature for 10 minutes. The colorimetric determination of nitrite concentration is measured by absorbance at 550 nm and quantified with a standard curve. The combination of LPS and interferon-γ produces a powerful stimulus for NO release in RAW264.5 macrophages. The effect of $\alpha_1$-antitrypsin in combination with 2,6,8-trihydroxypurine is compared to the effect of each agent individually.

6.4. Inhibition of INOS Induction

RAW 264.7 macrophage monolayers are treated for 1 hour with $\alpha_1$-antitrypsin (3 mg/ml), followed by costimulation by interferon-γ (10 U/ml), and LPS (1 ng/ml) for 18 hours. The cells are lysed by exposure to lysis solution (50 mm Tris-HCl, pH 8.0, 137 mm NaCl, 10% (v/v) glycerol, 1% (v/v), Nonidet P-40, 1 mM NaF, 10 μg/ml leupeptin, 10 mg/ml aprotinin, 2 mM sodium vanadate, and 1 mM phenylmethylsulfonyl fluoride). Samples containing equivalent amounts of total protein are subjected to SDS-polyacrylamide gel electrophoresis. Western blots of the gels are prepared, non-specific sites blocked by incubation overnight with 5% non-fat dry milk, and iNOS detected by incubation with iNOS anti-serum (Alexis Corporation, 1:1000 in 5% (w/v) bovine serum albumin in a solution of 20 mm Tris-HCl, pH 7.6, 137 mM MgCl, and 0.005% (v/v) Tween 20). Using horseradish peroxidase-conjugated second antibody, the antibody bound to iNOS is detected by enhanced chemiluminescence. The effect of the combination of interferon-γ, and LPS on induction of iNOS in the cell extract and the effect of pretreatment with $\alpha_1$-antitrypsin are measured.

6.5. $\alpha_1$-Antitrypsin in Experimental Allergic Encephalomyelitis

Induction of Experimental Allergic Encephalomyelitis (EAE), a model of multiple sclerosis, in rats by adoptive transfer of myelin basic protein (MBP)-specific T cells or in SJL or SWXJ-14 mice by immunization with MBP or proteolytic protein from the myelin sheath (PLP 139–151), a peptide derived from MBP, results in variable disease. The clinical symptoms of EAE are scored as tabulated below.

TABLE2

Severity Scores and Symptoms of Experimental Allergic Encephalomyelitis Score Clinical Symptoms 1 piloerection, tail weakness
2 tail paralysis
3 hind limb weakness/paralysis
4 hind and forelimb paralysis
5 moribund The severity of clinical symptoms of EAE is determined in relation to NO production in the CNS. The site of major NO production is known to vary between different EAE models. The adoptive transfer of MBP-specific T cells in Lewis rats causes NO production which is largely limited to the spinal cord while immunization of SWXJ-14 mice with PLP 139–151 results in the elaboration of high levels of NO in both spinal cord and brain. Mice (n=3) are treated beginning on day 5 post-immunization with 2 mg/mouse $\alpha_1$-antitrypsin twice daily i.p. and are continued until day 16 after the immunization. Mean severity scores are graded as detailed in Table 2.

6.6. $\alpha_1$-Antitrypsin Effect on N-CNOS and E-CNOS

A soluble cytosolic fraction of the rat cerebral cortex is used as a source of N-cNOS. An homogenate of bovine pulmonary arterial endothelium (BPAE) cells is used as a source of E-cNOS. The following NOS inhibitors are used as control compounds: L-NNA; $N^G$-nitro-L-arginine methyl ester (L-NAME); $N^G$-amino-L-arginine (L-AA); $N^G$-iminoethyl-ornithine (L-NIO); $N^G$-monomethyl-L-arginine (L-NMMA); $N^G$-allyl-L-arginine (L-ALA); and 7-nitroindazole (7-NI); aminoguanidine (AG). The N-cNOS crude enzyme is prepared by the following procedure. The whole brains of normal untreated male Sprague-Dawley (SD) rats weighing 300–400 g are homogenized for 3 min in 5 volumes of cold solution: 50 mM Tris-HCl containing 1 mM DTT (pH 7.4), followed by centrifugation at 1,000×g for 10 min. The supernatant is further centrifuged at 100,000×g for 60 min and a soluble cytosolic fraction of the finally obtained supernatant is used as the source of N-cNOS. The crude enzyme sample of E-cNOS is prepared by the following procedure. BPAE cells are cultured in MEM medium containing 20% of fetal bovine serum. When the cells are confluent, the cells are detached from the flask using a solution of 0.25% trypsin containing 1 mM EDTA in 0.1 M phosphate-buffered saline (PBS; pH 7.4) and centrifuged at 1,000 rpm for 5 min. The supernatant is discarded and upon addition of a suitable amount of PBS, centrifugation is performed at 1,000 rpm for 5 min to wash the cells. The same procedure is repeated using 50 mM Tris-HCl containing 1 mM DTT (pH 7.4) to wash the cells. To the precipitating cells, there is added 50 mM Tris-HCl containing 1 mM DTT (pH 7.4) and the mixture is homogenized for 3 min to yield the crude enzyme sample of E-cNOS. An inhibitor of serine proteases, e.g. (Benzyloxycarbonyl)-L-Valyl-N-[1-(3-(5-(3-Trifluoromethylbenzyl)-1,2,4-oxadiazolyl)carbonyl)-2-(S)-Methylpropyl]-L-Prolinamide; (5 mg/ml) or one of the control compounds, is added to the reaction solution, consisting of 100 nM L-[$^3$H] arginine, N-cNOS or E-cNOS as crude enzyme sample (6–20 μg/ml protein), 1.25 mM CaCl$_2$, 1 mM EDTA, 10 μg/ml calmodulin, 1 mM NADPH, 100 μM tetrahydrobiopterin, 10 μM FAD, 10 μM FMN and 50 mM Tris-HCl (pH 7.4). The reaction is started by adding the L-[$^3$H] arginine to the reaction solution and the mixture is incubated at 37° C. for 10 min. Incubation is terminated by addition of 2 ml of 50 mM Tris-HCl (pH 5.5) containing 1 mM EDTA. The reaction solution is quenched by placing the mixture on ice. The reaction solution is passed through a cation-exchange resin column (Dowex AG50WX-8, Na$^+$ form, 3.2 ml) and the reaction product L-[$^3$H] citrulline is separated from the unreacted residual substrate L-[$^3$H] arginine. The eluant is combined with another eluant resulting from the passage of distilled water (3 ml) through the column and put into a mini vial for recovery of L-[$^3$H] citrulline. Thereafter, 5 ml of a scintillation fluid is added and the contained radioactivity is measured with a liquid scintillation counter to determine the amount of L-[$^3$H] citrulline. The protein concentration of each crude enzyme sample is determined with a micro-assay kit of BioRad Co.

6.7. An in Vitro Model for Septic Shock

The effects of the agents AAT, (Benzyloxycarbonyl)-L-Valyl-N-[1-(3-(5-(3-Trifluoromethylbenzyl)-1,2,4-oxadiazolyl)carbonyl)-2-(S)-Methylpropyl]-L-Prolinamide; (Benzyloxycarbonyl)-L-Valyl-N-[1-(3-(5-(2-Phenylethyl)-1,2,4-oxadiazolyl)carbonyl)-2-(S)-Methylpropyl]-L-Prolinamide; and (Benzyloxycarbonyl)-L-Valyl-N-[1-(3-(5-(2-Methoxybenzyl)-1,2,4-oxadiazolyl)carbonyl)-2-(S)-Methylpropyl]-L-Prolinamide for protection of mouse L929 cells from cytotoxic effects of TNF are evaluated as follows. L929 cells (10$^5$ cells/well) are treated with 300 ng/ml of human TNF with or without the agent (added one hour prior to TNF addition) at 0.03, 0.1, 0.3, 1.0, 3.0 and 10 mg agent/ml. One day later the cells are stained for viability using 2', 7'-bis(2-carboxyethyl)-5(6)'-carboxyfluorescein and fluorescence analyzed for viability using a Millipore fluorescence plate reader. The results are evaluated in terms of the dose response to the agent.

6.8. Effect of Protease Inhibitor Agents on γ-IFN Stimulation of Monocyte Production of Cytokines The effect of the agents AAT, (Benzyloxycarbonyl)-L-Valyl-N-[1-(3-(5-(3-Trifluoromethylbenzyl)-1,2,4-oxadiazolyl)carbonyl)-2-(S)-Methylpropyl]-L-Prolinamide; (Benzyloxycarbonyl)-L-Valyl-N-[1-(3-(5-(2-Phenylethyl)-1,2,4-oxadiazolyl)carbonyl)-2-(S)-Methylpropyl]-L-Prolinamide; (Benzyloxycarbonyl)-L-Valyl-N-[1-(3-(5-(2-Methoxybenzyl)-1,2,4-oxadiazolyl)carbonyl)-2-(S)-Methylpropyl]-L-Prolinamide; (3 mg/ml) on cytokine production by monocytes activated by γ-IFN (100 U/ml), or combinations of γ-IFN and LPS (1 μg/ml) is evaluated. HL-60 monocyte-like cells are aliquoted into microwell plates ($10^5$ cells/well) and treated in the presence of saline, γ-IFN (100 U/ml), LPS (1 μg/ml), or combinations of γ-IFN and LPS for 24 hrs at 37° C. The conditioned media are collected and assayed for interleukin (IL)-1 α, tumor necrosis factor (TNF)-α, and granulocyte-macrophage colony stimulating factor (GM-CSF) production by ELISA. The rank order of efficacy of the agents is determined for production of each cytokine.

6.9. Protease Inhibitor Agent Effects in LPS-Induced Inflammation

LPS (250 μg, E. coli K-235, Sigma cat. no. L-2018) is administered to normal BALB/c mice (female, 12 weeks) at time zero. One group of mice (50 animals) is then treated at 30 minute intervals by i.p. injections of bovine serum albumin (BSA) (Sigma cat. no. 6793) dissolved in pyrogen-free, sterile, isotonic water (2.5 mg BSA per animal per injection, each injection containing 100 μl). The second group of mice (50 animals) is treated at 30 minutes intervals by i.p. injections of (Benzyloxycarbonyl)-L-Valyl-N-[1-(3-(5-(3-Trifluoromethylbenzyl)-1,2,4-oxadiazolyl)carbonyl)-2-(S)-Methylpropyl]-L-Prolinamide dissolved in pyrogen-free, sterile, isotonic water (0.2 ml per animal per injection, each injection 3 mg/ml). Glucose levels are determined on blood samples at time zero and after 3 hours, as a measure of response to LPS and to the agent.

6.10. Effects of $\alpha_1$-Antitrypsin and (Benzyloxycarbonyl)-L-VALYL-N-[1-(3-(5-(3-Trifluoromethylbenzyl)-1,2,4-Oxadiazolyl)Carbonyl)-2-(S)-Methylpropyl]-L-Prolinamide in a Model of Encotoxemia Swiss-Webster mice 4–6 weeks of age (20–25 g) are divided into 5 groups: endotoxic mice (endotoxin 60 mg/kg i.p. in acute treatment); two groups of endotoxic mice treated with 3 injections of 100 μl $\alpha_1$-antitrypsin (5 minutes, 2 and 4 hours post administration of the endotoxin) at $\alpha_1$-antitrypsin concentrations of 5 mg/ml and 1 mg/ml, respectively; and two groups of endotoxic mice treated with 3 injections of 100 μl (Benzyloxycarbonyl)-L-Valyl-N-[1-(3-(5-(3-Trifluoromethylbenzyl)-1,2,4-oxadiazolyl) carbonyl)-2-(S)-Methylpropyl]-L-Prolinamide (5 minutes, 2 and 4 hours post administration of the endotoxin) at agent concentrations of 5 mg/ml and 1 mg/ml, respectively. The effect of the protease inhibitors on the survival rate, and on blood levels of malonyldialdehyde, glutathione, TNF-α, and IL-1α is measured.

6.11. Effects of $\alpha_1$-Antitrypsin and Agent (Benzyloxycarbonyl)-L-VALYL-N-[1-(3-(5-(Difluoromethyl)-1,2,4-Oxadiazolyl) Carbonyl)-2-(S)-Methylpropyl]-L-Prolinamide in a Model of Septic Shock Peritonitis is induced in rats (Sprague-Dawley, male, 200–225 g each) in the following way. A one cm incision is made into the peritoneum to expose the cecum. A tight ligature is placed around the cecum with 4-0 suture distal to the insertion of the small bowel, forming an area of devitalized tissue while maintaining bowel continuity. A puncture wound is made with 16-gauge needle into the anti-mesenteric surface of the cecum and a small amount of fecal contents is expressed through the wound. The cecum is replaced into the peritoneal cavity, and the anterior peritoneal wall and skin are closed with surgical staples. Each animal is given a bolus of normal saline (15 ml/kg) for hydration and allowed to recover overnight. At 24 hours a schedule of treatment is initiated, with injections at 6 hr intervals. One group of animals is injected with 0.5 ml saline, another group is injected (i.p.) with 0.5 ml of $\alpha_1$-antitrypsin (5 mg/ml); and a third group is injected (i.p.) with 0.5 ml (Benzyloxycarbonyl)-L-Valyl-N-[1-(3-(5-(Difluoromethyl)-1,2,4-oxadiazolyl) carbonyl)-2-(S)-Methylpropyl]-L-Prolinamide (5 mg/ml). The seven-day survival rate is measured.

6.12. Modulation of Proteinase-activated Receptors

The invention also relates to the effect of $\alpha_1$-antitrypsin and $\alpha_1$-antitrypsin-like agents on the activation of proteinase-activated receptors (PARs). Alpha$_1$-antitrypsin and $\alpha_1$-antitrypsin-like agents block PAR activation and thereby reduce vasodilation mediated by NO, reduce extravasation of plasma proteins, decrease infiltration of immune cells, and block protease-stimulated mitosis. Thus the diseases described above in Section 5.5. can be treated with inhibitors of PAR, including, but not limited to, $\alpha_1$-antitrypsin, $\alpha_1$-antitrypsin-like agents, blocking antibodies, inhibitory kinases or kinase cDNA, inhibitory proteases, and hirudin. Inhibitory proteases can include any protease that cleaves the PAR at a site other than the activation site.

Throughout this application various publications and patents are referenced. The disclosures of these publications and patents in their entireties are hereby incorporated by reference into this application in order to more fully describe the state of the art to which this invention pertains.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A pharmaceutical composition comprising a therapeutically effective amount of at least one agent exhibiting mammalian $\alpha_1$-antitrypsin or $\alpha_1$-antitrypsin-like activity, and a therapeutically effective amount of at least one free radical scavenger, wherein the at least one free radical scavenger is 2,6,8-trihydroxypurine, dihydrorhodamine, or a combination thereof.

2. The pharmaceutical composition of claim 1, which further comprises a pharmaceutically acceptable carrier.

* * * * *